(12) United States Patent
Tyrrell et al.

(10) Patent No.: US 10,376,880 B2
(45) Date of Patent: Aug. 13, 2019

(54) LATERAL FLOW DEVICES AND METHODS OF MANUFACTURE AND USE

(71) Applicant: CAREHEALTH AMERICA CORPORATION, El Monte, CA (US)

(72) Inventors: Steven Patrick Tyrrell, Erie, CO (US); Dean Kingston, Arvada, CO (US)

(73) Assignee: CAREHEALTH AMERICA CORPORATION, El Monte, CA (US)

( * ) Notice: Subject to any disclaimer, the term of this patent is extended or adjusted under 35 U.S.C. 154(b) by 441 days.

(21) Appl. No.: 14/909,434

(22) PCT Filed: Jul. 30, 2014

(86) PCT No.: PCT/US2014/048987
§ 371 (c)(1),
(2) Date: Feb. 1, 2016

(87) PCT Pub. No.: WO2015/017591
PCT Pub. Date: Feb. 5, 2015

(65) Prior Publication Data
US 2016/0167042 A1    Jun. 16, 2016

Related U.S. Application Data

(60) Provisional application No. 61/860,232, filed on Jul. 30, 2013.

(51) Int. Cl.
*G01N 33/558* (2006.01)
*B01L 3/00* (2006.01)

(52) U.S. Cl.
CPC .......... *B01L 3/5023* (2013.01); *G01N 33/558* (2013.01); *B01L 2200/0605* (2013.01);
(Continued)

(58) Field of Classification Search
USPC ........................................................ 422/402
See application file for complete search history.

(56) References Cited

U.S. PATENT DOCUMENTS 5,863,502 A * 1/1999 Southgate ............ B01J 19/0046
422/417
5,976,895 A    11/1999 Cipkowski
(Continued)

FOREIGN PATENT DOCUMENTS

EP          2302363         3/2011
WO    WO2010/021873        2/2010
WO    WO2012/012500        1/2012

*Primary Examiner* — Jill A Warden
*Assistant Examiner* — Brittany I Fisher
(74) *Attorney, Agent, or Firm* — Scully, Scott, Murphy & Presser, P.C.

(57) ABSTRACT

A lateral flow assay test device providing a structure for the lateral flow assay reactions provides for a continuous flow path of bibulous material provided in separate but contiguous regions of the device in which the bibulous layers are in fluid contact with each other thereby providing flow control of the timing and speed of the assay reaction. Increased flow control results in increasing reliability of use, increasing sophistication of reactions and increases the range of molecules or diagnosis that can be identified. Such flow control can extend processing times and allow users or test givers to manually delay test processing providing enhanced test results.

6 Claims, 7 Drawing Sheets

(52) U.S. Cl.
CPC ............... *B01L 2200/0647* (2013.01); *B01L 2200/0684* (2013.01); *B01L 2200/0689* (2013.01); *B01L 2200/148* (2013.01); *B01L 2300/021* (2013.01); *B01L 2300/023* (2013.01); *B01L 2300/024* (2013.01); *B01L 2300/041* (2013.01); *B01L 2300/069* (2013.01); *B01L 2300/0825* (2013.01); *B01L 2300/0887* (2013.01); *B01L 2300/126* (2013.01); *B01L 2300/161* (2013.01); *B01L 2400/0406* (2013.01); *B01L 2400/0694* (2013.01); *B01L 2400/086* (2013.01); *G01N 2333/59* (2013.01)

(56) References Cited

U.S. PATENT DOCUMENTS

| | | | |
|---|---|---|---|
| 6,293,012 B1 * | 9/2001 | Moles | B01L 3/502707 29/890.124 |
| 6,365,417 B1 * | 4/2002 | Fleming | G01N 33/558 422/412 |
| 6,372,516 B1 * | 4/2002 | Sun | B01L 3/5023 422/408 |
| 7,133,545 B2 | 11/2006 | Douglass et al. | |
| 7,605,004 B2 | 10/2009 | Zhou | |
| 7,943,381 B2 | 5/2011 | Lappe et al. | |
| 8,046,175 B2 | 10/2011 | Kuo et al. | |
| 8,367,013 B2 | 2/2013 | Kaylor et al. | |
| 2005/0089449 A1 * | 4/2005 | Polwart | B01L 3/502707 422/400 |
| 2005/0208593 A1 | 9/2005 | Vail et al. | |
| 2005/0277202 A1 * | 12/2005 | Fleming | G01N 33/558 436/514 |
| 2006/0008920 A1 * | 1/2006 | Wong | G01N 33/523 436/514 |
| 2006/0160078 A1 * | 7/2006 | Cardy | B01L 3/5023 435/6.11 |
| 2009/0208920 A1 * | 8/2009 | Ohman | B01L 3/502746 435/2 |
| 2011/0000610 A1 * | 1/2011 | Burke | G01N 33/558 156/269 |
| 2012/0052595 A1 * | 3/2012 | Wallace | G01N 33/558 436/501 |
| 2013/0100462 A1 | 4/2013 | Hollenbeck et al. | |
| 2013/0162981 A1 | 6/2013 | Emeric et al. | |

* cited by examiner

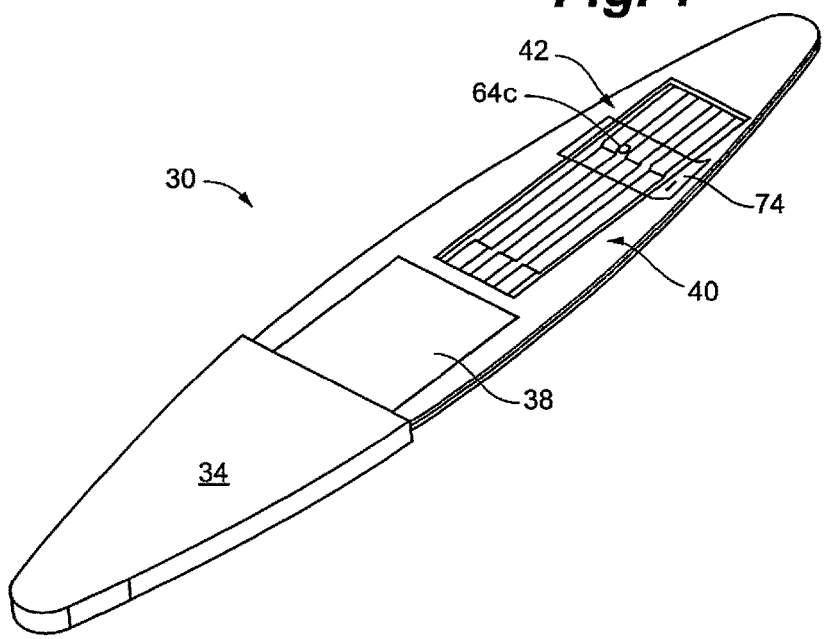
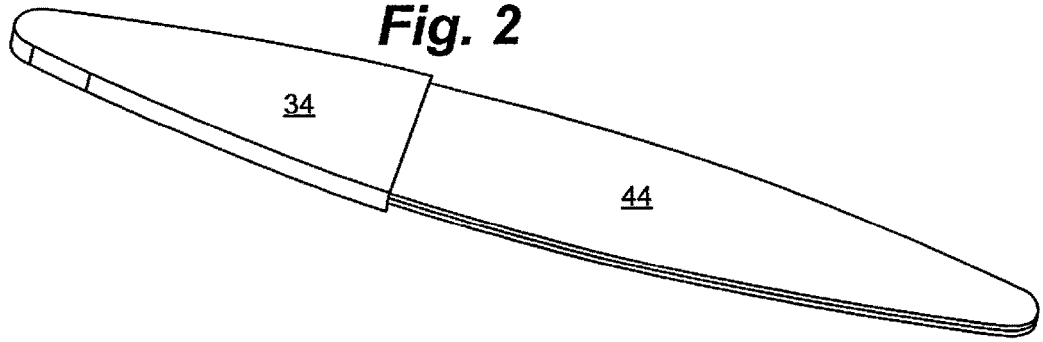
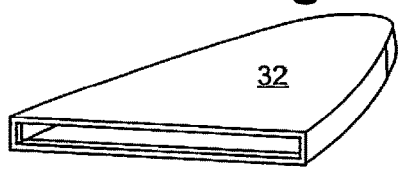

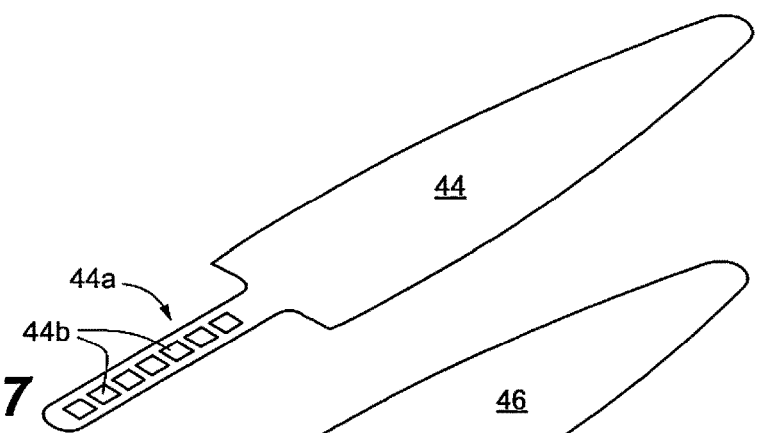
*Fig. 7*
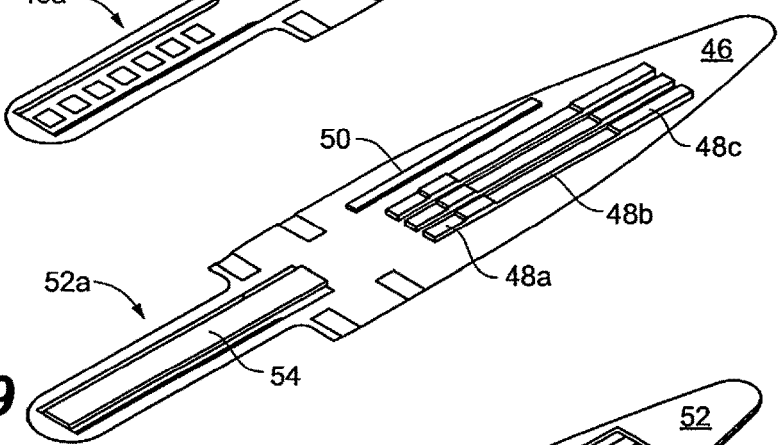
*Fig. 8*
*Fig. 9*
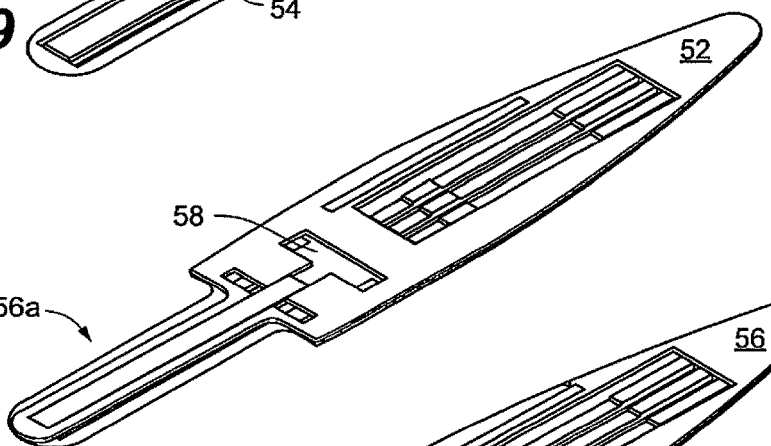
*Fig. 10*
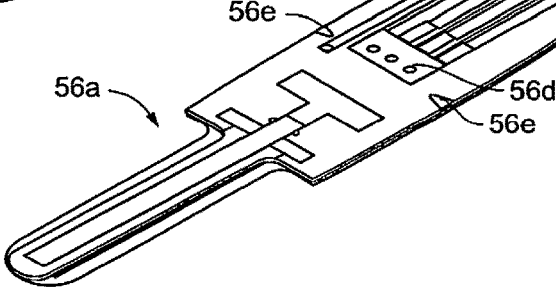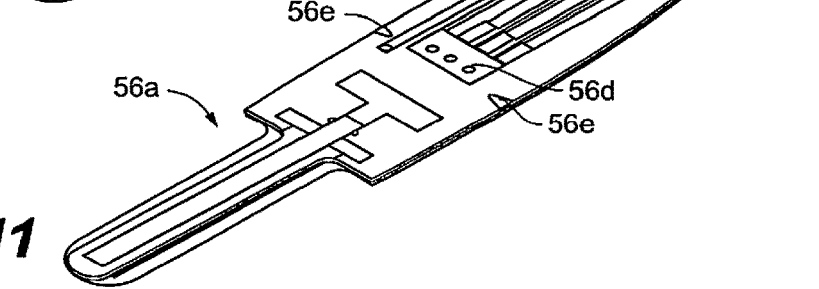
*Fig. 11*

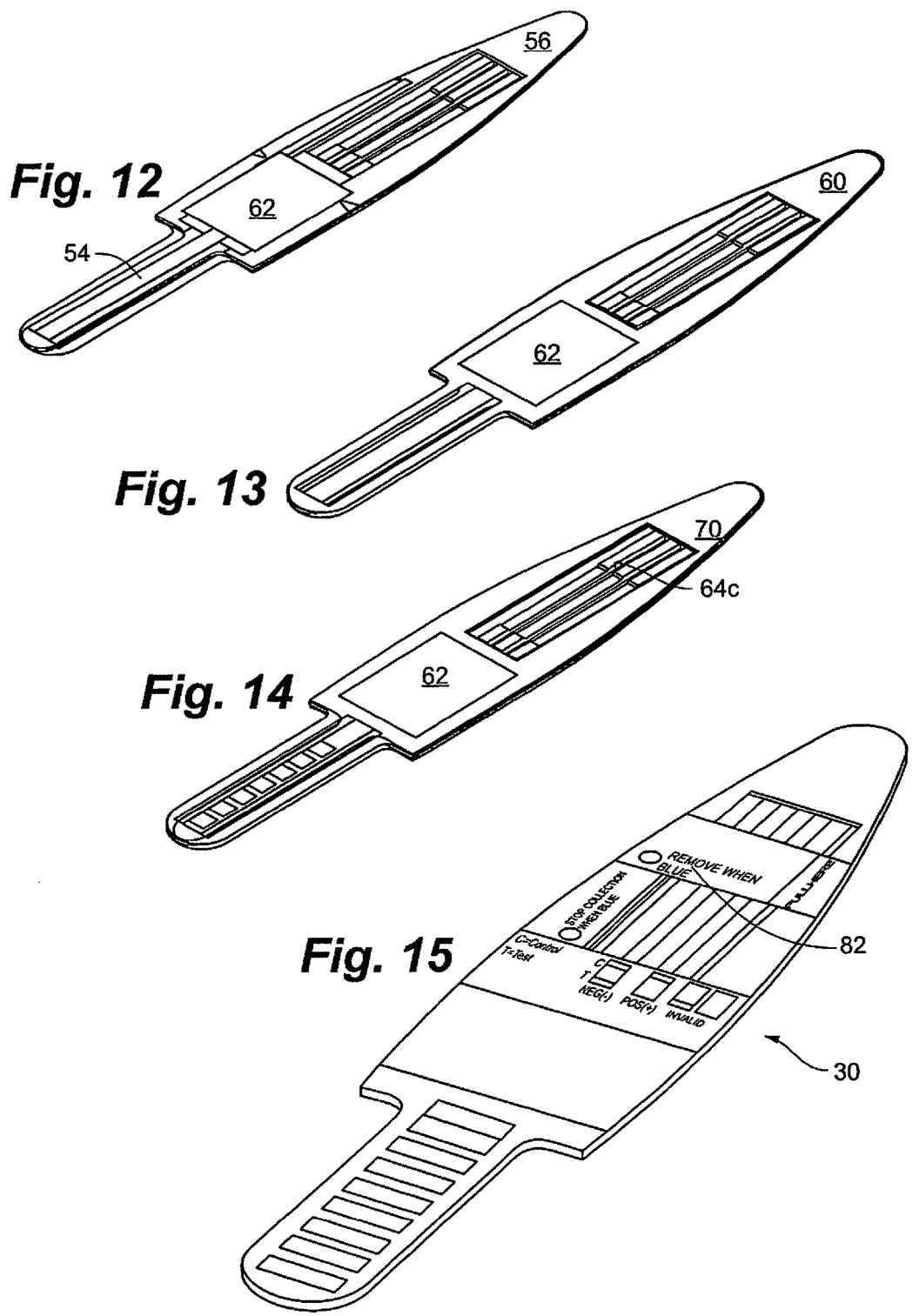

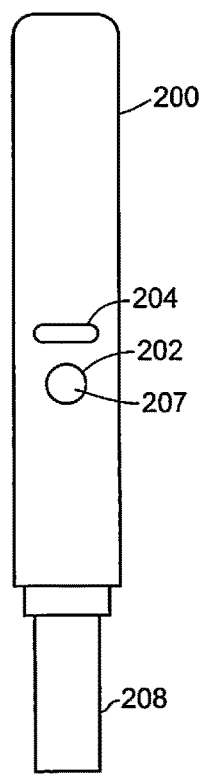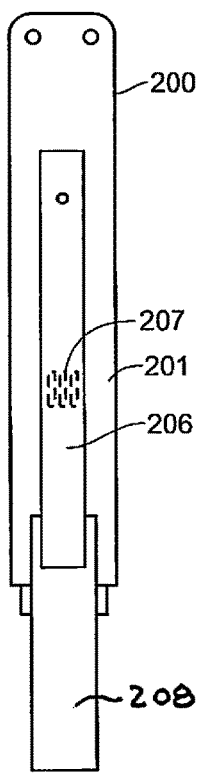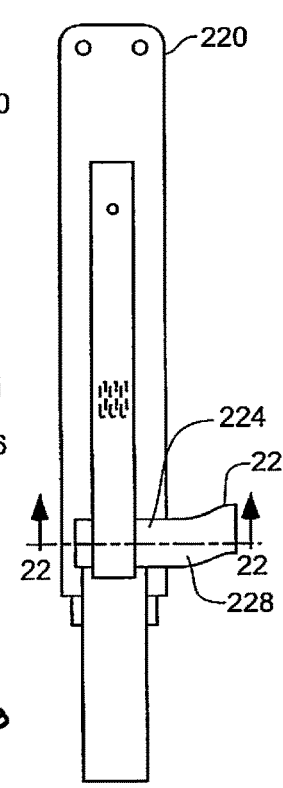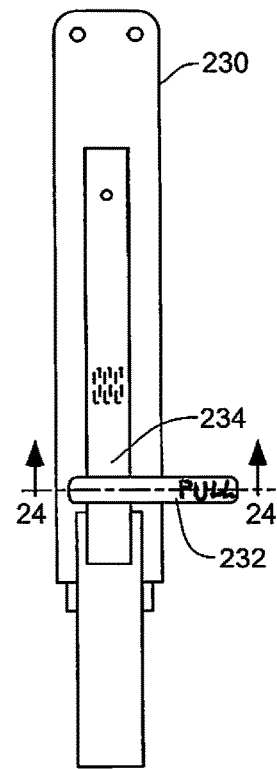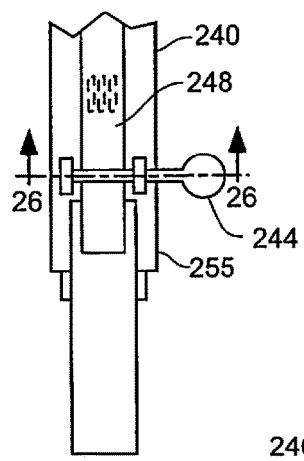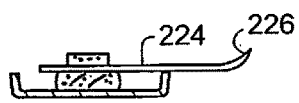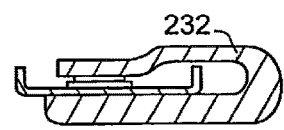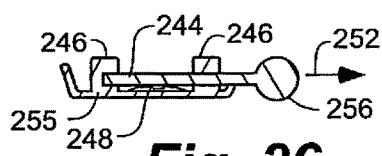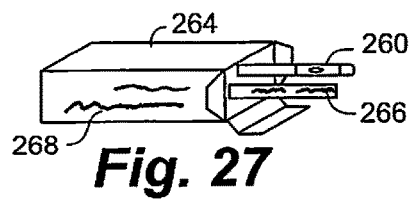

LATERAL FLOW DEVICES AND METHODS OF MANUFACTURE AND USE

RELATED APPLICATIONS

The present application is a National Phase entry of PCT Application No. PCT/US2014/048987, filed Jul. 30, 2014, which claims priority to U.S. Provisional Application No. 61/860,232, filed Jul. 30, 2013, the disclosures of which are incorporated by reference in their entirety.

FIELD OF THE DISCLOSURE

The disclosure relates generally to the field of manufacturing of a testing device incorporating a lateral flow drug test strip for testing individuals for diagnosis, clinical monitoring, or amounts of drugs or compounds, or metabolites thereof.

BACKGROUND

Immunoassays are particularly useful for their speed and specificity. Immunoassays make use of the specificity of antibodies and/or immunoglobulins to particular molecules. Recent technology has allowed immunoassays to be miniaturized and compartmentalized so as to be usable as test strips by easily used unskilled or non-healthcare workers to diagnose diseases, medical conditions and/or the presence of metabolites. Traditional test strips use techniques of chromatography to separate components as a solvent front moves upward through a substrate. However such "paper" chromatography provides separation of components in a sample does not provide specificity in identifying those components.

More recently, test strips have been designed to use the forces of capillary action to move the solvent front laterally, across the length of a test strip. Such "lateral flow" test strips increase the ease of use of such strips and by utilizing lateral flow are able to provide a platform for holding the assay components, in micromolar quantities dried along the length of the substrate to provide specific identification of molecules in a sample. Because of their ease of use and reliability lateral flow test strips are widely used in the field and by non-laboratory personnel to provide reliable data on the presence of drugs, chemicals and metabolites in a sample. A widely spread and well known application is the home pregnancy test.

Lateral flow assays make use of the force of capillary action to draw a solvent, in a lateral fashion through capillary beds formed in or on a substrate through a series of active regions on the test strip to provide a complete immuno assay reaction and provide a recognizable result at the other end of the test strip by the time the solvent/reaction has reached the end of the strip.

The typical test strip includes a series of active regions or elements that provide various components of the assay. Generally, the first element or portion includes a sample pad which acts as a sponge and holds an excess of sample fluid (such as urine, blood, plasma or saliva). Once the sample pad is wetted by the sample the fluid migrates to the second element or portion (conjugate pad) on which has been immobilized various reagents and/or bioactive particles needed to carry out the immunoassay, such reagents and/or bioactive particles include salts and or sugars to provide a proper pH, antibodies to a specific antigen, or antigens to a specific antibody. As the solvent front moves along the flow path, it dissolves the immobilized reagents and brings them in contact with particular proteins and/or molecules in the sample. The solvent front then carrying the immunoreaction then moves to a third area, often referred to as the stripes where a third molecule binds to the antibody/antigen complex. This third molecule is often a visual signal such that the reaction changes color upon reaching the stripes. Oftentimes the third area includes at least two stripes. One denoting a positive reaction and a second denoting a negative reaction. In some cases, there may be a positive control stripe (signifying that the reaction worked as intended), a negative control stripe (indicating that the reaction did not work and should be redone), a positive outcome stripe and a negative outcome stripe. Beyond the stripe region there is typically a further absorbent material which acts as a wick to remove and absorb any remaining fluid.

While current lateral flow assays have proven extremely useful and reliable, the suffer in their ability to support more sophisticated assays requiring increased incubations times, positive and/or negative controls and consequent reliability in results and field use and variation in molecules the assays are useful for.

Numerous systems and instruments have been created to aid in the detection of illegal drugs or compounds in persons suspected of imbibing, ingesting, injecting, or inhaling illegal or controlled drugs or compounds. These systems have been created for use in the fields of law enforcement, employment screening, and emergency medical treatment. These systems range from handheld portable single use devices to specimen containers that are analyzed with laboratory equipment. There is a need for single use disposable test devices that can be used for the analysis of more than one target compound, that can be visually read and also readable by electronic readers, and that provide enhanced accuracy, ease of use and low cost.

Known lateral flow assay test devices suitable for field use do not have the accuracy and low point detection that laboratory equipment provides. One reason for this is that the laboratory setting allows for the technician to perform multiple steps and extend and precisely time incubation and sample conditioning times. Such is not conducive to field use and use by untrained personnel. It would be very advantageous of some of the functionalities of the laboratory setting could be adapted to field use by untrained personnel thus providing enhanced accuracy and low point detection, particularly of drugs of abuse.

Moreover, existing disposable single use devices lack flexibility in activating the test processes. The test process starts when the sample is received in the lateral flow assay test device. Delaying the start of the test processing could be very useful, such as where a sample or group of samples are taken and the test giver wishes to delay the device processing and the reading. For example, it would be expedient to provide tests to groups of individuals serially and delay the activation of the test device process until the group has been tested. Such would save considerable time for each of the test subjects and be more efficient for the test administrators. Current disposable devices do not readily have such capability. Such devices need to be easily visually readable and inexpensive.

Moreover, such devices should be able to be manufactured utilizing known high speed manufacturing techniques such as described in U.S. Pat. Pubs. 2012/0061010 and 2007/0040567; U.S. Pat. No. 8,119,414;

SUMMARY

The present invention provides lateral flow assay test devices providing a structure for the lateral flow assay reactions provides for a continuous flow path of bibulous material provided in separate but contiguous regions of the device in which the bibulous layers are in fluid contact with each other thereby providing flow control of the timing and speed of the assay reaction. Increased flow control results in increasing reliability of use, increasing sophistication of reactions and increases the range of molecules or diagnosis that can be identified Therefore, in one exemplary embodiment, the invention provides an elongate lateral flow assay testing device comprising a body, the body including a proximal sample receiving end and a distal result display region at an opposite end. In various exemplary embodiments, the device also includes a plurality of laminated layers including a top layer and a bottom layer and plurality of window frame layers sandwiched therebetween. The plurality of window frame layers define a plurality of interconnected containment regions or flow channels whereby sample fluid can flow from the sample receiving end toward the opposite end. In some exemplary embodiments the regions comprising the body include: (a) a sample receiving region with a wick therein, the sample receiving region at the sample receiving end; (b) a conditioning region downstream from and adjacent to the sample receiving region, the conditioning region having a conditioning pad therein; (c) a reaction region with bibulous material downstream and adjacent to the conditioning region; and (d) a diagnostic result display region with bibulous material downstream and adjacent to the reaction region.

In various exemplary embodiments, the testing device further comprises a movable thin film impeding member in a laminated engagement with the body creating a sample fluid flow stop upstream of the diagnostic result display region. In these exemplary embodiments, the thin film impeding member is movable from an impeding position to a lesser impeding position whereby in the lesser impeding position the fluid flow moves beyond the fluid flow stop toward the diagnostic result display region.

In these and other exemplary embodiments, the fluid flow stop of the elongate lateral flow assay testing device is provided by a vent positioned upstream from the diagnostic result display region and the diagnostic display region is hermetically sealed downstream from the stop. In these exemplary embodiments, the sample fluid flow is impeded from flowing into the diagnostic display region. In these embodiments, the body has a vent extending into the reaction region and the thin film impeding member is seals and is removably engaged with the body covering the vent. In some embodiments, the thin film impeding member may be peeled off, opening the vent and allowing the sample fluid flow into the diagnostic result display region completing the reaction and providing visual result indication.

In various exemplary embodiments of the elongate lateral flow assay testing device, the fluid flow stop is positioned upstream of the reaction region and the reaction region and the diagnostic result display region are contiguous.

In some exemplary embodiments, the elongate lateral flow assay testing device includes a fluid flow path as defined from the wick to the conditioning pad to the bibulous material in the reaction region to the bibulous material in the diagnostic display region. In these embodiments the thin film impeding member is in the fluid flow path intermediate to the sample receiving region and the diagnostic result display region thereby defining the impeding position. In these embodiments the removal of the thin film impeding member out of the fluid flow path defines the lesser impeding position.

In yet other exemplary embodiments, the invention provides a lateral flow assay testing device including, (i) an elongated containment with a fluid sample receiving end, an opposite end; (ii) a bibulous sample receiving material exposed at the sample receiving end; a bibulous fluid sample processing material extending from the bibulous sample receiving material and extending lengthwise in the containment to a visual signal generating portion and defining a processing fluid flow path; a separate elongate bibulous timer material connecting to the sample receiving material and having a fluid sample flow controlled portion and a visual signal generating portion opposite the flow controlled portion for generating a time signal after a time delay; and a switch initially set to one of impede or interrupt the processing fluid flow path, the switch manually switchable to a position providing increased fluid flow in the processing flow path.

In these and other exemplary embodiments of the invention, a portion of the bibulous fluid sample processing material has a needed processing time and the separate elongate bibulous timer material is configured for providing the time signal a period of time at least equal to the needed processing time after the sample receiving material receives a fluid sample. In various exemplary embodiments of the lateral flow assay testing device the switch comprises a removable vent closure sealing a vent that extends from an interior compartment containing a portion of the fluid flow path. In some embodiments the vent closure comprises a film piece peelably removable from an exterior surface of the containment. In some embodiments, the switch comprises a member extending into and interrupting the processing flow path, the member retractable from the processing flow path by a portion exteriorly actuatable with respect to the containment.

In some exemplary embodiments of the invention, the switch comprises a thin film member positioned in between and two portions of confronting bibulous material whereby when the thin film is in place the fluid sample is at least substantially blocked from flowing between the two portions and when the thin film member is removed the fluid sample has an increased flow capability between the two portions. In this and other embodiments, the switch comprises a thin film member movable between an impeding position and a less impeding position in the processing fluid flow path.

In still other exemplary embodiments, the invention provides a lateral flow assay testing device comprising: (i) an elongated containment with a fluid sample receiving end, an opposite end; (ii) a bibulous sample receiving material exposed at the sample receiving end; (iii) a bibulous fluid sample processing material extending from the bibulous sample receiving material and extending lengthwise in the containment to a visual signal generating portion defining a fluid sample processing flow path; and (iv) a timer actuatable with a visually readable portion on the containment, receiving material for actuation when a sample is received at the sample receiving material, the timer having a visual signal generating portion opposite the flow controlled portion for providing a visual signal after a time delay, the timer having a bibulous timing material and a fluid sample timer flow path separate from the fluid sample processing flow path.

In various exemplary embodiments, the invention may also include a switch initially set to one of impede or interrupt the processing fluid flow path, the switch manually switchable to a position providing increased fluid flow in the processing flow path. In some exemplary embodiments, the timer is configured or configurable for providing visual signal a period of time at least equal to the needed processing time after the sample receiving material receives a fluid sample. In some embodiments, the switch comprises a removable vent closure sealing a vent that extends from an interior compartment containing a portion of the fluid flow path.

In yet other exemplary embodiments, the invention provides a lateral flow assay testing device comprising: (i) an elongated containment with a fluid sample receiving end, an opposite end; (ii) an elongated containment with a fluid sample receiving end, an opposite end; (iii) a bibulous sample receiving material exposed at the sample receiving end; (iii) a bibulous fluid sample processing material extending from the bibulous sample receiving material and extending lengthwise in the containment to a visual signal generating portion and defining a processing fluid flow path; and a removable blocking member positioned to interrupt the processing fluid flow path, the blocking member having a portion exposed exteriorly of the containment for actuation. In some exemplary embodiments the lateral flow testing device also provides a portion exposed exteriorly of the containment for actuation is configured as a pull tab.

In yet another exemplary embodiment, the invention provides a method of assembling a lateral flow assay test device comprising: (i) layering one or more framing layers over a base layer to define a window for receiving a bibulous pad, the window having a depth; (ii) inserting an uncompressed bibulous pad with a height that is greater than the depth of the window on the base and seating the pad on the base layer; (iii) layering a cover layer over the window with the pad therein thereby compressing at least a portion of the bibulous pad; and (iii) laminating together the base layer, one or more framing layers, and cover layers.

In various exemplary embodiments of the method according to the invention, the method also includes providing that the depth of the window is 90 percent or more than the height of the uncompressed bibulous pad. In some exemplary embodiments, the method also includes the bibulous pad is a first bibulous pad and a second bibulous pad is placed on the cover layer at the opening and the second bibulous pad is in fluid communication with the first bibulous pad. In some exemplary embodiments, the method also includes wherein the bibulous pad is a first bibulous pad and a second bibulous pad is placed on the cover layer at the opening and the second bibulous pad further comprising adding an additional framed layer for surrounding the second bibulous pad and an additional cover layer that provides a containment for the second bibulous layer, the second bibulous layer being compressed by the second framed layer whereby the first bibulous pad and second bibulous pad extend toward each other in the opening.

In embodiments of the invention, a laminated lateral flow assay test device has a timer. The test device receives a specimen, for example saliva, in a specimen receiving region at which point the specimen conventionally begins to flow down a flow path comprising bibulous material to a conditioning region; additionally, the timer is actuated as the specimen is received in the receiving region. The timer provides a timed delay and a visual indication, a signal, of when sufficient conditioning of the specimen has occurred. The test giver can then activate a manual actuator integrated with the device that further releases specimen fluid flow towards the test result display region where further test processes may occur and/or the test result may be visually read. In embodiments, the timer comprises a separate flow path from the flow path of the specimen to the conditioning region and the flow of the specimen is controlled corresponding to the desired delay such that after a predetermined delay, the specimen reaches a color changing region and the color change is the signal. In embodiments, the timer flow path may also include a sufficiency indicator that provides a signal when sufficient specimen has been received. So for example with a saliva test device, when the sufficiency signal is generated, the device may be removed from the test subject's mouth.

In embodiments, the manual actuator may be a vent closure of a flow path with the vent at or downstream of the test result indication region. The flow path isolated from the ambient atmosphere from a fluid flow stop point to the test result indication region whereby the capillary or wicking effect of the fluid in the bibulous material is muted or stopped. The stop point may be a vent at or just downstream of the conditioning portion. In embodiments, the vent closure may be a film that is secured with adhesive or otherwise secured to a vent port, sealingly closing the vent port. Manual retraction of the film then opens the vent port. Suitable instructions may be placed directly on the film actuator. In embodiments of the invention, a film actuator may extend into the specimen flow path and separate two portions of bibulous material such that when the film is pulled the flow path is completed.

In embodiments, the manual actuator may be a clamping member that compresses the bibulous material constituting the flow path to the test result display region. Removal of the clamp then allows the bibulous material to uncompress and the flow of the specimen fluid continues to the test result indication region.

In embodiments of the invention, a laminated lateral flow assay test device has a flow path that extends from a specimen receiving region to a conditioning region to a test result display region. The flow path has a film laminate that functions as a flow interrupter member that delays the processing and completion of the test of the device. When removed or moved the film laminate allows specimen fluid flow to extend to test processing regions and/or the test result display region. The film laminate may be a film adhered to a vent port sealingly closing the vent port, the vent port the only opening to the atmosphere of flow path downstream of a stop point, the stop point positioned at or downstream of the conditioning region and the stop point may be defined by a vent.

In embodiments, the initial stop point may be a first vent or a restriction of the flow path.

In embodiments, a laminated lateral flow assay test device is manufactured by roller laminate presses and including cutting and placing of the film flow interrupter member. Such may be placed with adhesive over a layer comprising a vent. Or the interrupter member may be, inserted between overlapping or in between otherwise abutting bibulous portions defining flow path portions.

Methods of making laminated testing devices are provided for use in testing for diagnosing, monitoring, or measuring chemical or other parameters relating to disease or medical conditions, or for detecting or measuring the presence of illegal or prohibited drugs, compounds or metabolites, wherein the test strip is manufactured to be used out of the packaging by non-technically trained users, and can be manufactured using high speed roller laminate presses at higher speed and/or cost than known methods.

The method can provide continuous manufacturing a laminate testing device for diagnostic, clinical or drug testing using high speed web presses, reels or rollers, and die cutters, said method comprising:

a. providing a plurality of rolls or strips of layers on high speed web press reels or rollers, each layer comprising at least one of (i) a test strip layer, (ii) a hydrophobic substrate layer; and (iii) a hydrophobic adhesive layer, two or more of said layers provided on a plurality of roller sheets, and two or more of said layers having a first surface defined by an adhesive layer;

b. positioning the said first adhesive surface of one layer faces the first adhesive surface of another layer; and c. laminating and die cutting, using a high speed web reel or roller conveyer system that is controlled by a programmed computer, said reels or rollers comprising feed and waste reels or rollers comprising said rolls or strips of said layers, along with die cutters, said plurality of layers such that the components provided by said plurality of layers are formed into at least a portion of said multilayer testing device from said multilayer strip laminate and adhesive surfaces of different of said layers;

wherein during steps (a), (b), and (c), said test strip is compressed less than 5-10 percent;

wherein one or more of said hydrophobic substrate, test strip or hydrophobic adhesive layers comprise at least one or more of one or more test strips, a top layer/casing with at least one sample application window, a sample preparation or dry buffer or conditioner area of the one or more test strips, a first compartment template casing with one or more spacers, assay path channels, a first bottom casing template, and a sample application compartment, provided as components of said multilayer laminate testing device; and wherein said high speed web conveyer system moves one or more of said layers in said step (c) in said high speed web conveyer system at a speed greater than 10 feet per minute.

Non limiting optional embodiments can include devices, methods of making or using, software, computer readable computer systems, and/or systems for testing for or detecting the presence of drugs or other chemicals or metabolites, e.g., but not limited to, diagnosing, monitoring, or measuring chemical or other parameters relating to disease or medical conditions, or for testing for illegal or prohibited drugs, optionally in non-controlled or difficult to control environments.

A device, method or system can optionally use one or more of oral fluids (e.g., saliva), and/or other tissue or bodily fluids (e.g., but not limited to, urine, blood or plasma) as the test sample. Non limiting optional embodiments can optionally include one or more of an electronic device such as a smart phone or other wireless, internet or cellular communications capable device, in combination with digital and/or other imaging, data processing, data storage and/or wireless electronic transmission of data via cellular networks or Wi-Fi.

A device, system or method can optionally collect, detect, process, manipulate, alter, condition, determine, validate, and/or test oral or other bodily fluids or tissues in volumes sufficient for testing, chemically and/or mechanically collecting, detecting, processing, manipulating, altering, conditioning, determining, validating, and/or testing the one or more of an oral or other bodily fluid or tissue. A device, system or method can further provide for the set up and/or optimize for testing and/or delivering the conditioned fluids to lateral flow test strips or other testing systems for diagnosing, monitoring, or measuring chemical or other parameters relating to disease or medical conditions, or for determination of the presence or absence, or other quantitative or qualitative measurement, of specific and/or selected drugs, chemicals or biological materials, such as illegal or prohibited drugs or compounds.

Such devices can also optionally provide for timing the test endpoint and/or subsequent image capture by either automatic initiation of timing once the testing device is inserted into the positioning case of by the user initiating the start time of the test by interacting with a touch sensitive or other graphical user interface.

A lateral flow test strip device, system or method can optionally provide wherein the person performing the test (tester) performs at least one selected from the group consisting of removing the test device from the packaging, removing a cap from an fluid collecting device or placing the fluid collecting device in a test subject's mouth.

These and other features and advantages of various exemplary embodiments of the devices and methods according to this invention are described in, or are apparent from, the following detailed description of various exemplary embodiments of the methods according to this invention.

BRIEF DESCRIPTION OF THE DRAWINGS

FIG. 1 is a top plan perspective view of one exemplary embodiment of a lateral flow testing device according to one exemplary embodiment of the invention;

FIG. 2 is a bottom plan perspective view of the exemplary embodiment of the lateral flow testing device according to the exemplary embodiment of the invention shown in FIG. 1.

FIG. 3 is a side perspective view of a cover for a lateral flow testing device as shown in FIGS. 1 and 2.

FIGS. 7-15 illustrate the individual layers of one exemplary embodiment of a lateral flow testing device as shown in FIG. 6.

FIG. 7 shows a first layer or platform for the lateral flow testing device.

FIG. 8 shows a second layer of the lateral flow testing device overlaid on the first layer.

FIG. 9 shows various reaction members of the lateral flow testing device placed in working orientation on the substrate according to this exemplary embodiment of the invention.

FIG. 10 shows a third layer or frame laid on top of the reaction members of FIG. 9.

FIG. 11 should a fourth layer or flow through window place on top of the channel frame/third layer of FIG. 10.

FIG. 12 illustrates a conditioning pad aligned with the wick on the fourth layer/frame FIG. 13 shows a fifth layer or frame covering the conditioning pad.

FIG. 14 shows a layer covering the fifth layer and a vent hole present in the layer above the result display region.

FIG. 15 shows peel away instructions and film provided on the fifth layer and covering the vent.

FIG. 19 is a prior art consumer lateral flow assay test device for HCG detection, known as a pregnancy test.

FIG. 20 is a the prior art device of FIG. 19 with the top cover removed disclosing the bibulous sample collection portion and the bibulous processing portion.

FIG. 21 is an interrupter or delay mechanism comprising a thin film in accord with embodiments of the invention herein.

FIG. 22 is a cross sectional taken at line 22-22 of FIG. 21.

FIG. 23 is an interrupter or delay mechanism configured as a C-shaped clamp in accord with embodiments of the invention herein.

FIG. 24 is a cross sectional taken at line 24-24 of FIG. 23.

FIG. 25 is an interrupter or delay mechanism configured as a rigid member in accord with embodiments of the invention herein.

FIG. 26 is a cross sectional taken at line 26-26 of FIG. 25.

FIG. 27 is a perspective view of a packaged device according to embodiments of the invention.

DESCRIPTION

Figure 4:
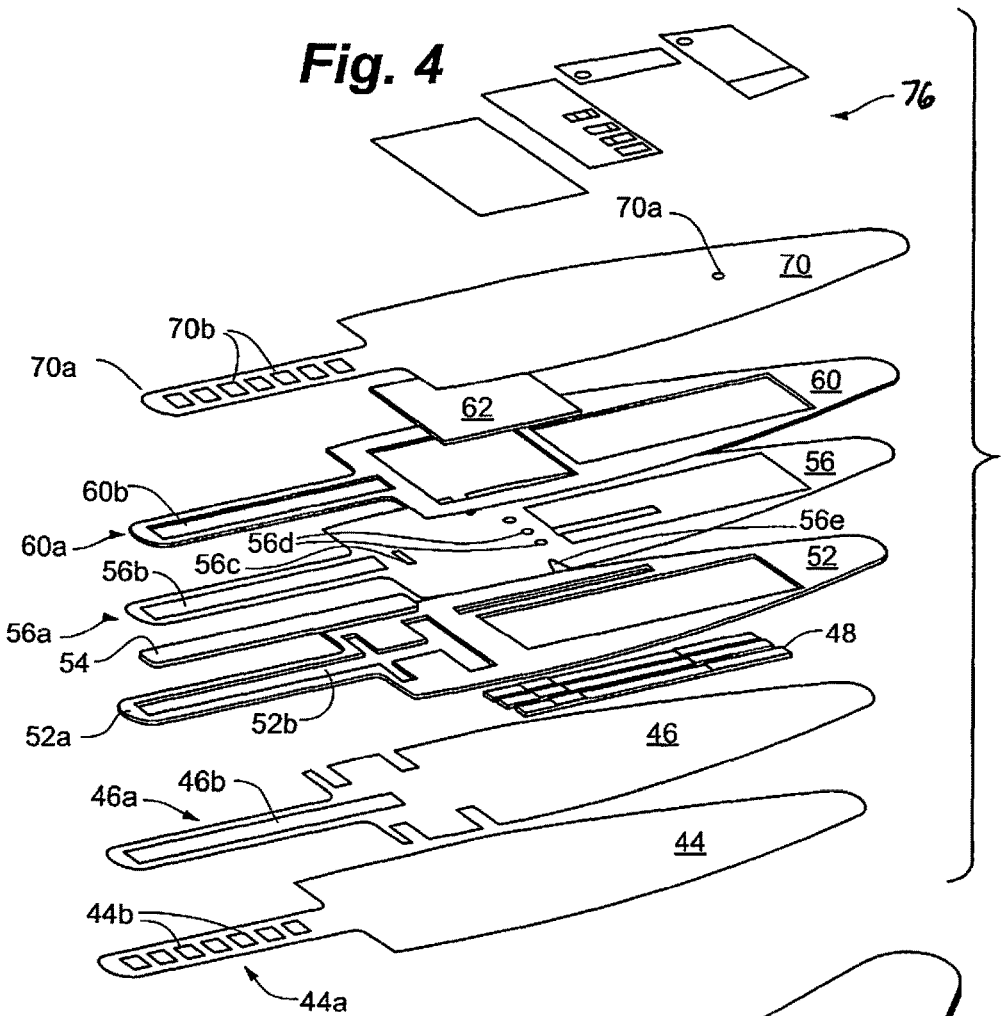
FIG. 4 is an exploded perspective view of an exemplary embodiment of a lateral flow testing device according to the invention.

The present disclosure is directed, in general, to lateral assay test devices, to methods of making, providing and/or using, particularly for, saliva, urine, or body fluids. Also, lateral flow test strip systems, It has been unexpectedly discovered that one or more aspects of the design, content, components, orientations, compression, adhesives, plastics, roller systems and methods, contacts, fluidic contacts, shapes, sizes, dimensions, holes, cutting, slits, overlays, venting, timing, control, and/or other aspects of the materials, components, manufacturing methods and structures, provide results that are unexpected, synergistic, taught away, advantageous, lower cost, more accurate, more reproducible, more consistent, provide precise volume control and/or accuracy, provide more reproducible and accurate results at lower cost and/or faster production, as described herein optionally with what is known in the art.

Non limiting optional embodiments of the present invention are based the discovery and engineering of improved test strips and manufacturing methods as described herein and known in the art. It has not unexpectedly been found, or taught away from, including but not limited to, one or more the following, as non limiting examples:

Capillary Force Driven—

Capillary force driven migration can be controlled by one or more of various methods useful in interrupting the capillary flow of the solvent/test fluid including opening or closing an external vent, imposition of a soluble membrane along the flow path, imposition of a non-soluble but removable membrane along the flow path, decreasing the capillary force by compressing the capillary bed and limiting the flow path. Such devices can be incorporated into the assay test strip during manufacture. For example, as a closed vent can cause air pressure to build in the device as fluid flows in thus displacing the air in a sealed chamber. Opening an external vent releases this pressure enabling flow to continue. Automatic closing can be accomplished by position vents at positions where the sample fluid flow is stopped as desired and calibrated positions to provide one or more of accuracy, consistency, incubation time, pre-calibration, faster manufacture, or cheaper manufacture. Dissolvable membranes can be employed to stop flow until the membrane dissolves to provide one or more of accuracy, consistency, incubation time, pre-calibration, faster manufacture, or cheaper manufacture. As a non-limiting example, such a vent can be designed and/or made to close an air passage when wetted since the air pressure generated within a compartment by capillary force driven liquid flow low enough so as to not be sufficient to force air through a wet material, wherein this can be used to stop flow passively and automatically at a time determined only by the flow rate of a fluid moving towards a valve and the distance on flow. Such features can optionally be used as a fluidically controlled stop or start switch.

Passive Volume Control:

Capillary driven fill can be governed by size of the materials that exhibit capillary forces towards aqueous materials. The volume of the materials can be very tightly controlled the height of the compartment that the material resides in since this laminated assembly may have precise vertical dimensionality, e.g., within at least one of 0.1-5 percent variation; Flow stops when the materials are saturated with fluid. Materials are surrounded by hydrophobic materials to ensure there is no flow outside the materials that support capillary force driven flow.

Fluidic contacts between materials can be made by placing holes in the laminated liquid tight layers instead of the typical overlapping approached used for lateral flow rapid test strips yielding more precise fluid transfer volumes. When the flow is directed to move from a transport material positioned below a second transport material and these two materials are connected by a hole in one of the laminated layers, this ensures that all flow is driven by capillary forces and not by fluidic head pressure. Using these techniques, fluid can be made to enter a transport material at very precise locations as opposed to dipping a test strip in a fluid.

Labeling can be registered to critical components within the assembled device. This significantly minimizes registration errors.

Open space compartments with hydrophilic surfaces can be designed into the device. These are essentially capillary tubes. These spaces fill from the proximal point of sample application to the most distal portion. When the test strip or other fluidic components are positioned at the distal end of these compartments or channels, this channel serves as a fluidic metering device thus ensuring that a testing process will not begin until the channel is full and there is sufficient sample volume to complete a testing process.

An optional embodiment of a fluid collection and/or testing device can optionally collect fluids from the fluids of the person being tested by absorption driven by capillary forces native to the specified absorptive materials, wherein the device can optionally have an indicator that changes color or provides an visual, mechanical, or electrical indicator when the device is full of, or has sufficient, fluid to conduct the selected test. This indicator can also serve as a passive timer for chemically conditioning the fluid since dissolution of the dried chemicals and/or action of these chemicals on the components of the fluid is not an instantaneous process and/or can require some time to optimally condition the fluid instead of personnel person supervising the testing or providing the timing, such open compartments can optionally be included as a feature of the testing device itself. This timing can be varied, as a non-limiting example, by changing the distance of migration or the materials supporting migration to reach an optimal time for conditioning.

Sample Entry Control and Preparation, Flow Control, and Venting.

A feature of the testing device, as provided in non-limiting optional embodiments, is that introduction of the unconditioned fluid to the lateral flow test strips can optionally not occur until sufficient incubation time has elapsed and/or a label or sticker is removed from the device. As the device is filling with or collecting fluid, the fluid can enter a region containing conditioning chemicals and/or buffers. A testing device can optionally contain one or more capillary force based and/or shaped compartments, that can optionally be functionally air tight from the outside environment when fluids are introduced to the device, thus, unless a vent is added, provided, or activated, such as with vent holes provided in the device, flow can be interrupted or shifted to another capillary bed with an uninterrupted flow path. In order for fluid to optionally flow into the materials included in each compartment, a vent to the outside can optionally be present to allow air displacement by the entering fluid. If the vent is not present or open fluid may optionally not enter the compartment by capillary forces alone. By opening the vent, such as by removing a sticker, cover or the like over the vent of the chamber(s) within the later flow test strips, the user can optionally control when the fluid enters this chamber. In various exemplary embodiments, a testing initiation sticker covering one or more vents in a test strip chamber can only be removed when the device indicates sufficient fluid has been collected and/or because preset, passive timing events have elapsed, indicating that the fluid has been conditioned. Such conditioning means that the test fluid/sample has mixed with the reagents or the conditioning chemicals before some indicator indicates "full" and/or would then be in an optimal state for lateral flow testing.

Prior art references disclosing flow control in lateral flow assay test devices include: U.S. Pat. Nos. 5,620,657; 5,705, 397; 6,901,963; 7,803,319 and U.S. Patent Publications 2002/0119486; 2010/0159599; 2011/0306072, all of which are incorporated by reference.

Optional functions of non-limiting optional embodiments can include one or more of:
1. Collection of bodily fluids and/or ensuring that the filling of the internal compartments of the testing device only occurs through capillary forces generated by the liquid interacting with the transport materials incorporated within the device. No test subject generated pressure of vacuum effects.
2. Ensuring that the fluid spends a set or minimum time with the fluid conditioning chemicals.
3. A fill indicator can optionally serve two purposes.
   a. Indicate that sufficient fluid has been collected to ensure that the device has sufficient sample to complete testing.
      i. A time required to fill is optionally and not directly related to the time it takes for the indicator to indicate a full state. A observed fill time can be artificially extended to ensure that fluid has incubated with the conditioning chemicals a sufficient amount of time. This can optionally be accomplished by the choice of materials in the fill indicating area since these can be chosen based on lateral flow rates thus impacting the observed fill time. This can also be optionally accomplished by simply lengthening the migration distance of the fluid in the fill indicator area to modify the observed fill time.
4. An optional removable cover, sticker or the like or incorporated vent hole can, when present, prevent the flow of fluid onto the later flow test strip and/or permit the flow of fluid onto the lateral flow test strips when removed opened or closed.
   a. Controlling fluid flow rates in the lateral flow testing devices. A precise nature of the laminated structure can apply very precise pressure to the reagent test strip or pads of the lateral flow test strip thus compressing the pad slightly but limiting the amount of compression and/or slowing and/or the flow rates into the lateral flow test strip providing more time and/or optimization for indicator reactions to occur.
   b. Flow rates within lots of test strips can be variable due to variable densities of reagent pads. Compressing these pads to the same height with a limited and/or precise amount of volume compression has been discovered to improve flow rate consistency.

The test strip can optionally analyze the presence or amount of a drug, compound, or metabolite thereof in a bodily fluid or tissue to determine whether said amount is above a pre-selected threshold or concentration, or to provide a reading of result quantitatively.

The term "component" can refer, but is not limited to designated selected regions, such as edges, corners, sides or the like; structural members, such as strips, pads, layers or panels, layers of material, or the like.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a test strip that is placed with or near the element, formed or applied within a layer of the element or another test strip, or other variations or combinations thereof.

The various parts of the test strip can be attached to one another or associated with one another to form a structure that preferably maintains its shape during the useful life of the test strip. As used herein, the terms "attached," "joined," "associated," and similar terms encompass configurations whereby a first part is directly joined to a second part by affixing the first part directly to the second part, by indirectly joining the first part to the second part through intermediate members, and by fixing the relative positions of various parts by capturing parts between other parts. Those skilled in the art will appreciate that various methods or combinations of methods may be used to securely join the respective parts of the test strip to one another.

General Process Description:

This method, including non limiting optional embodiments as taught herein and/or as known in the relevant arts, can be summarized, as non-limiting examples, as optionally including one or more of:

a method can provide continuous manufacturing a laminate testing device for diagnostic, clinical or drug testing using high speed web presses, reels or rollers, and die cutters, said method comprising:

a. providing a plurality of rolls or strips of layers on high speed web press reels or rollers, each layer comprising at least one of (i) a test strip layer, (ii) a hydrophobic substrate layer; and (iii) a hydrophobic adhesive layer, two or more of said layers provided on a plurality of roller sheets, and two or more of said layers having a first surface defined by an adhesive layer;

b. positioning the said first adhesive surface of one layer faces the first adhesive surface of another layer; and c. laminating and die cutting, using a high speed web reel or roller conveyer system that is controlled by a programmed computer, said reels or rollers comprising feed and waste reels or rollers comprising said rolls or strips of said layers, along with die cutters, said plurality of layers such that the components provided by said plurality of layers are formed into at least a portion of said multilayer testing device from said multilayer strip laminate and adhesive surfaces of different of said layers;

optionally wherein during steps (a), (b), and (c), said test strip is compressed less than 5-10 percent;

optionally wherein one or more of said hydrophobic substrate, test strip or hydrophobic adhesive layers comprise at least one or more of: one or more test strips, a top layer/casing with at least one sample application window, a sample preparation or dry buffer or conditioner area of the one or more test strips, a first compartment template casing with one or more spacers, assay path channels, a first bottom casing template, and a sample application compartment, provided as components of said multilayer laminate testing device;

optionally wherein said high speed web conveyer system moves one or more of said layers in said step (c) in said high speed web conveyer system at a speed greater than 10 feet per minute;

optionally wherein one or more of said layers (i), (ii) and (iii) is provided with a backing layer or liner that can be added or removed prior to said laminating step (c);

optionally wherein said method further comprises, prior to step (c), laminating a backing film, liner, or hydrophobic polymer to said adhesive layer; optionally wherein the number of one of (i) a test strip layer, (ii) a hydrophobic substrate layer and (iii) an adhesive layer is selected from 1, 2, 3, 4, 5, 6, 7, 8, 9, or 10 layers, e.g., wherein the total number of laminated adhesive layers is at least two;

optionally wherein said die cutting or laminating provides one or more selected from (a) vent holes, (b) fluid transport control holes; (c) assay path channels; (d) sample application window or compartment; (e) sample preparation areas or compartment; (f) a detection area or compartment; (g) and dissolvable membranes, one or more connected to adjacent layers, components, or compartments, in one or more layers or surfaces of said laminate testing device;

optionally wherein one or more of said vent holes (a) stops flow of fluid in said test strip when the fluid in the test strip comes in contact with the vent hole; or (b) provides optimized or predetermined capillary flow of fluid through the laminate testing device;

optionally wherein said fluid transport control holes allow and control fluid flow between layers or sections of test strip or adjacent compartments in said test strip to increase capillary driven flow and decrease flow by fluidic head pressure;

optionally wherein said capillary flow is maximized and said flow by fluidic head pressure is minimized;

optionally wherein said dissolvable membranes delay flow of fluid until the membrane dissolves to regulate the position or timing of fluid flow through the laminate testing device;

optionally wherein the laminating or die cutting results in the formation of open space compartments in said laminate testing device that hold one or more of a fluid, a test strip, a channel, or a vent;

optionally wherein said open space compartment provides a channel for application of a fluid sample to be tested, wherein the channel is provided adjacent to the proximal end of the test strip and the fluid is held in the channel until a pre-determined amount of fluid accumulates and is then released into the adjacent test strip or that the fluid enters the test strip at a pre-determined location;

optionally wherein the distal end of the test strip has a substantially flat end that provides a visual indication of the end of the fluid flow within the test strip, stops the flow of the fluid, or provides a location for the result indicator for use of the test strip;

optionally wherein at least a portion of the volume of the open space compartments in said laminate testing device is produced with less than 0.01 to 5 percent variance;

optionally wherein said method further comprises provided a calibrated or scaled label to said laminate testing device that indicates calibration or qualitative or quantitative results for the use of said laminate testing device;

optionally wherein said test strip is enclosed by two or more of said hydrophobic polymer and adhesive layers in said laminate testing device provided by step (c);

optionally wherein said test strip is substantially surrounded by a raised border made of hydrophobic adhesive;

optionally wherein, during steps a, b, and c, said test strip is compressed less than 2-10 percent;

optionally wherein said test strip comprises nitrocellulose;

optionally wherein said nitrocellulose has a pore size of about 1-12 microns; optionally wherein said pore size is about 8-12 microns;

optionally wherein said resultant laminate testing device provides pre-calibrated lateral flow test strips comprising or provided with soluble or dry buffers for preparing a liquid biological fluid or tissue sample from a person being tested that is applied to one or more of said resultant multilayer test strips;

optionally wherein said test strip comprises an indicator for a drug or compound selected from alcohol, cocaine, methamphetamine, heroin, THC, PCP, psilocybin, an opiate drug, or derivatives thereof;

optionally wherein the resultant laminate testing device has a first release liner defining a first outer surface, a second release liner defining a second outer surface, and the plurality of layers are positioned between the first and second release liners;

optionally wherein one or more of said hydrophobic, test strip or adhesive layers comprises at least one or more of: a top layer/casing with at least one sample application window, a sample preparation/dry buffer/conditioner strip, a first compartment template casing, an assay path channel, a first bottom casing template, as components of said multilayer laminate testing device;

optionally wherein said transparent top layer/casing, sample preparation/dry buffer/conditioner strip, first compartment template casing, second compartment template casing, third compartment template casing comprise a sample buffer/conditioning manifold;

optionally wherein said sample/buffer/conditioning manifold is in fluid communication with said assay path channels first bottom casing template;

optionally wherein said hydrophobic adhesive comprises an acrylic solvent based or rubber based adhesive;

optionally wherein said test strip comprises an indicator for diagnosis, treatment, or clinical monitoring of a medical condition;

optionally wherein one or more of said steps (a), (b), and (c) are repeated one to ten times to form a portion of said multilayer laminate testing device;

optionally wherein, prior to repeating one or more of said steps (a), (b), and (c), one or more of the portions of said multilayer laminate testing device provided in step (c) are rolled or re-rolled up to form one or more re-rolled layers of one or more said combined one or more of said layers (i), (ii) and (iii), which rolled layers are then provided according to step (a), (b), or (c);

optionally wherein said one or more re-rolled layers are provided with a backing layer or liner that can be added or removed prior to the repeating of one or more of said steps (a), (b), or (c);

wherein one or more of said reels or rollers are fed with processor tension control of layer, component, test strip, membrane or other web material for one or more of coating, adhesive, cutting, forming, shaping, as part of one or more of steps (a), (b), and (c);

optionally wherein, during one or more of steps (a), (b), and (c), reagent, test strip, substrate, adhesive, or other material or component is provided using a reel to reel or roller to roller positive or negative displacement system for providing, guiding, supplying, laminating or cutting at high speed web, test strip provision, feeding, cutting, preparation, impregnation, or lamination;

optionally wherein said displacement system provides said web, test strip provision, feeding, cutting, preparation, or lamination at a web speed of 2-500 feet per minute;

optionally wherein said web speed is selected from the group consisting of 2-10, 5-10, 5-25, 20-40, 3-7, 25-50, 25-75, 25-100, 25-50, 40-60, 20-45, 75-150, and 100-200 feet per minute;

optionally wherein said displacement system provides processor controlled automatic tracking of providing, guiding, supplying, impregnating, laminating or cutting positions on the web or layer;

optionally wherein said method further includes web speed control or orientation of primary or secondary web layers, components, test strips, test strips with backing, liner or card, or materials, said speed, orientation control for one or more of the main or secondary web conveyers;

optionally wherein said method further comprises reel or roller tension control, monitoring, adjustment, cutting or die cutting or take-up, of web, conveyer, layer, or test strip with backing, liner or card, with automatic web, conveyer, layer, component, or test strip tracking;

optionally wherein said method further comprises layer or component tolerances relative to a reference, of 0.01-5 percent average or mean variation;

optionally wherein said tolerance is selected from the group consisting of 01-3, 0.5-2, 0.1-2, 0.6-0.1, 0.8-1.2, 0.9-1.1 percent average or mean variation;

optionally wherein said fluid transport control holes are laminated in step (c) using said test strip layers having a backing or liner that enhance speed of said web above 5 feet per second or a tolerance of thickness of the test strip to less than 5 percent variance per 100 testing devices produced by said method;

optionally wherein said adjacent compartments in said test strip vary in thickness or height in said test device by less than 5 percent variance per 100 testing devices produced by said method.

The method can optionally further provide wherein the resultant laminate testing device provides pre-calibrated lateral flow test strips comprising or provided with soluble or dry buffers for preparing a liquid biological fluid or tissue sample from a person being tested that is applied to one or more of the resultant multilayer test strips;

optionally wherein said testing device further comprises a hydrophilic adhesive that contributes to one or more of the rate, placement, or direction of flow of said biological sample within said assay path channels, holes, vents, or guides within the testing device, such as, but not limited to increasing, decreasing, modifying, controlling, and/or facilitating the rate, placement, or direction of flow of said biological sample within one or more of said assay path channels, holes, vents, or guides within the testing device;

optionally wherein the method or system manufactures or produces at least 25, 50, 75, 80, 85, 90, 95, 100, 110, 120, 125, 130, 140, 150, 175, 200, 250, 300, 400, or 500 partial or complete testing devices per minute, and/or 1000, 1500, 2000, 2500, 3000, 4000, 5000, 6000, 7000, 7500, 8000, 9000, 10,000, 12,500 or 15,000 partial or complete testing devices per hour.

The method can optionally further provide wherein substrate comprises an indicator for a drug or compound selected from alcohol, cocaine, methamphetamine, heroin, THC, PCP, psilocybin, an opiate drug, or derivatives thereof.

The method can optionally further provide wherein the resultant laminate testing device has a first release liner defining a first outer surface, a second release liner defining a second outer surface, and the plurality of layers are positioned between the first and second release liners.

The method can optionally further provide wherein one or more of the hydrophobic, substrate or adhesive layers comprises at least one or more of: a top layer/casing with at least one sample application window, a sample preparation/dry buffer/conditioner strip, a first compartment template casing, an assay path channel, a first bottom casing template, as components of the multilayer laminate testing device. The method can optionally further provide wherein the top layer/casing, sample preparation/dry buffer/conditioner strip, first compartment template casing, second compartment template casing, third compartment template casing comprise a sample buffer/conditioning manifold. The method can optionally further provide wherein the sample/buffer/conditioning manifold is in fluid communication with the assay path channels first bottom casing template.

Prior art references disclosing manufacturing techniques and methods relevant include U.S. Pat. Nos. 8,506,903; 8,119,414; and Publications 2007/0040567; 2012/0061018. Said patents and publications are incorporated herein by reference.

Test Strip Features and Components:

A lateral flow testing device of non limiting optional embodiments made according to the invention can be of any shape and dimensions, such as one or a combination of square, round, oval, polygonal, hexagonal, and the like, but preferably is a rectangular test strip.

A test strip of a test device of the non-limiting optional embodiments made according to the invention may comprise as comprising the substrate, at least in part, any bibulous or non-bibulous material, such as nitrocellulose, nylon, paper, glass fiber, dacron, polyester, polyethylene, olefin, or other cast or thermoplastic materials such as polyvinyl chloride, polyvinyl acetate, copolymers of vinyl acetate and vinyl chloride, polyamide, polycarbonate, polystyrene, etc. In a preferred embodiment, at least one test strip material is nitrocellulose having a pore size of at least about 1 micron, more preferably of greater than about 5 microns, or about 8-12 microns. Suitable nitrocellulose sheets having a nominal pore size of up to approximately 12 microns, are available commercially from, for example, Schleicher and Schuell GmbH.

A test strip used in context with the non-limiting optional embodiments can optionally include indicia that can include a designation for the test to be performed using the test strip. Such indicia may be printed on the test strip material using methods known in the art. Alternatively, indicia may be on other thin members, such as plastic or paper, that are attached to the test strip, such as by adhesives, tape or the like.

A test strip can include one or more materials. If a test strip comprises more than one material, the one or more materials are preferably in fluid communication. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and may or may not partially overlap one another.

A material or materials of the test strip can be bound to a support or solid surface such as found, for example, in thin-layer chromatography and may have an absorbent pad either as an integral part or in liquid contact. For example, a test strip may comprise nitrocellulose sheet "backed", for example with a supporting sheet, such as a plastic sheet, to increase its handling strength. This can be manufactured by forming a thin layer of nitrocellulose on a sheet of backing material. The actual pore size of the nitrocellulose when backed in this manner will tend to be lower than that of the corresponding unbacked material. Alternatively, a preformed sheet of nitrocellulose and/or one or more other bibulous or non-bibulous materials can be attached to at least one supporting sheet, such as a sheet made of polymers (see, e.g., U.S. Pat. No. 5,656,503, entirely incorporated by reference herein). A supporting sheet can be transparent, translucent or opaque. In aspects of the non-limiting optional embodiments where the support sheet is transparent, the supporting sheet is preferably moisture impervious but can be moisture resistant or moisture pervious. In the non-limiting optional embodiments the test strip can be viewed through a window comprised of a transparent material such as glass, plastic, or mylar, but preferably break resistant.

In the following discussion, strips of test strip material will be described by way of illustration and not limitation.

Generally, test strips of the non-limiting optional embodiments include a sample application zone and a test results determination region. A test results determination region can include either or both of one of more drug, compound, or metabolite detection zones and one or more control zones. Optionally, a test strip can include a reagent zone. One or more specific binding members in the test results determination region of the test strip can be impregnated throughout the thickness of the substrate as a bibulous or non-bibulous material in the test results determination region (for example, specific binding members for one or more drugs, compound, or metabolite can be impregnated throughout the thickness of the test strip material in one or more drug, compound, or metabolite detection zones, and specific binding members for one or more control drugs, compound, or metabolite can be impregnated throughout the thickness of the test strip material in one or more control zones, but that need not be the case). Such impregnation can enhance the extent to which the immobilized reagent can capture a drug, compound, or metabolite present in the migrating sample. Alternatively, reagents, including specific binding members and components of signal producing systems may be applied to the surface of the bibulous or non-bibulous material. Impregnation of specific binding members into test strip materials or application of specific binding members onto test strip materials may be done manually or by machine.

Nitrocellulose has the advantage that a specific binding member in the test results determination zone can be immobilized without prior chemical treatment. If the porous solid phase material comprises paper, for example, the immobilization of the antibody in the test results determination zone can be performed by chemical coupling using, for example, CNBr, carbonyldiimidazole, or tresyl chloride.

Following the application of a specific binding member to the test results determination zone, the remainder of the porous solid phase material should be treated to block any remaining binding sites elsewhere. Blocking can be achieved by treatment with protein (for example bovine serum albumin or milk protein), or with polyvinylalcohol or ethanolamine, or any combination of these agents. A labeled reagent for the reagent zone can then be dispensed onto the dry carrier and will become mobile in the carrier when in the moist state. Between each of these various process steps (sensitization, application of unlabeled reagent, blocking and application of labeled reagent), the porous solid phase material should be dried.

To assist the free mobility of the labeled reagent when the test strip is moistened with the sample, the labeled reagent can be applied to the bibulous or non-bibulous material as a surface layer, rather than being impregnated in the thickness of the bibulous material. This can minimize interaction between the bibulous or non-bibulous material and the labeled reagent. For example, the bibulous or non-bibulous material can be pre-treated with a glazing material in the region to which the labeled reagent is to be applied. Glazing can be achieved, for example, by depositing an aqueous sugar or cellulose solution, for example of sucrose or lactose, on the carrier at the relevant portion, and drying (U.S. Pat. No. 5,656,503). A labeled reagent can then be applied to the glazed portion. A remainder of the carrier material should not be glazed.

Reagents can be applied to the carrier material in a variety of ways. Various "printing" techniques have previously been used or known in the art for application of liquid reagents to carriers, for example micro-syringes, pens using metered pumps, direct printing and ink-jet printing, and any of these techniques can be used in the present context. To facilitate manufacture, the carrier (for example sheet) can be treated with the reagents and then subdivided into one or more of smaller portions, layers, components, laminates, or other structures (for example small narrow strips each embodying the required reagent-containing zones) to provide a plurality of identical carrier units.

In embodiments where the medical tested substance, drug, compound, or metabolite is detected by a signal producing system, such as by one or more enzymes that specifically react with the analyte, one or more components of the signal producing system can be bound to the medical tested substance, drug, compound, or metabolite detection zone of the test strip material in the same manner as specific binding members are bound to the test strip material, as described above. Alternatively or in addition, components of the signal producing system that are included in the sample application zone, the reagent zone, or the medical tested substance, drug, compound, or metabolite detection zone of the test strip, or that are included throughout the test strip, may be impregnated into one or more materials of the test strip. This can be achieved either by surface application of solutions of such components or by immersion of the one or more test strip materials into solutions of such components. Following one or more applications or one or more immersions, the test strip material is dried. Alternatively or in addition, components of the signal producing system that are included in the sample application zone, the reagent zone, or the medical tested substance, drug, compound, or metabolite detection zone of the test strip, or that are included throughout the test strip, may be applied to the surface of one or more test strip materials of the test strip as was described for labeled reagents.

Sample Application Zone

A sample application region or zone is an area of a test strip where a sample, including fluid samples, such as a biological fluid sample such as blood, serum, saliva, or urine, or a fluid derived from a biological sample, such as a throat or genital swab, is applied. A sample application zone can include a bibulous or non-bibulous material, such as filter paper, nitrocellulose, glass fibers, polyester or other appropriate materials. One or more materials of the sample application zone may perform a filtering function, such that large particles or cells are prevented from moving through the test strip. A sample application zone can be in direct or indirect fluid communication with the remainder of the test strip, including the test results determination zone. A direct or indirect fluid communication can be, for example, end-to-end communication, overlap communication, or overlap or end-to-end communication that involves another element, such as a fluid communication structure such as filter paper.

A sample application zone or other part of the substrate can also optionally include compounds or molecules that may be necessary or desirable for testing and/or optimal performance of the test. The sample application zone or substrate can optionally include, for example, but not limited to, one or more of added, pre-added or post-added buffers, stabilizers, surfactants, salts, reducing agents, affinity agents, labels, enzymes, indicators, binding agents, a labeled agent or specific binding member, such as antibodies or active fragments thereof attached or linked to a label, or the like, which can be made using methods known in the art. A specific binding member can bind a drug, compound, tissue, biological component, or metabolite and/or can bind an optional compound, or the like.

Reagent Zone

A test strip can also include a reagent zone where reagents useful in the detection of a drug, compound, or metabolite can be provided immobilized (covalent or non-covalent immobilization) or not immobilized, particularly when in a fluid state. A reagent zone can be on a reagent pad, a separate segment of substrate, e.g., comprising a bibulous or non-bibulous material included on the test strip, or it can be a region of a bibulous or non-bibulous material of a test strip that also includes other zones, such as a drug, compound, or metabolite detection zone. In one aspect of non-limiting optional embodiments, the reagent zone or substrate can optionally include, for example, but not limited to, one or more of added, pre-added or post-added buffers, stabilizers, surfactants, salts, reducing agents, affinity agents, labels, enzymes, indicators, binding agents, a labeled agent or specific binding member, such as antibodies or active fragments thereof attached or linked to a label, or the like, which can be made using methods known in the art. A specific binding member can bind a drug, compound, tissue, biological component, or metabolite and/or can bind an optional compound, or the like.

In one example, the reagent zone can include two or more populations of colored beads. One population of colored beads is attached to an anti-rabbit IgG antibody or active fragment thereof and the other population of colored beads is attached to an anti-drug, compound, or metabolite antibody or active fragment thereof. A labeled anti-rabbit IgG antibody or antibody fragment is used for visual detection of a signal in the control zone of the test strip. A color signal in the control zone indicated that the sample has passed through the detection zone. A labeled anti-drug, compound, or metabolite antibody or fragment thereof provides a visual signal in the detection zone indicating the presence of drug, compound, or metabolite in the sample.

Other preferred embodiments are having anti-(drug of abuse) antibodies or active fragments thereof bound to a population of colored beads. More than one population of beads can be used as in the forgoing example to provide a visual signal in the detection zone and a second visual signal in the control zone. A two populations of beads can be the same or are different colors or be provided as a mixture of colors. Alternatively or in addition, different populations of beads bound to different antibodies or antibody fragments can be used to indicate the presence of more than one drug, compound, or metabolite in a sample by producing one or more visual signals in one or more detection zones. The detection zone or substrate can optionally include, for example, but not limited to, one or more of added, pre-added or post-added buffers, stabilizers, surfactants, salts, reducing agents, affinity agents, labels, enzymes, indicators, binding agents, a labeled agent or specific binding member, such as antibodies or active fragments thereof attached or linked to a label, or the like, which can be made using methods known in the art. A specific binding member can bind a drug, compound, tissue, biological component, or metabolite and/or can bind an optional compound, or the like.

In another aspect of non-limiting optional embodiments, the reagent zone includes the medical tested substance, drug, compound, or metabolite or a drug, compound, or metabolite analog, bound to a population of colored beads. In this case, the medical tested substance, drug, compound, or metabolite in the sample competes with the labeled drug, compound, or metabolite or drug, compound, or metabolite analog provided in the reagent zone for binding to a specific binding member in the test results determination zone. A reduced visual signal in comparison with an optional sample lacking drug, compound, or metabolite indicates the presence of drug, compound, or metabolite in the sample. More than one population of beads can be used as in the forgoing examples to provide a visual signal in the medical tested substance, drug, compound, or metabolite detection zone and a second visual signal in the control zone. Alternatively or in addition, different populations of beads bound to different drugs, compound, or metabolite or drug, compound, or metabolite analogs can be used to indicate the presence of more than one drug, compound, or metabolite in a sample by producing one or more visual signals in one or more detection zones.

Preferred labels are beads such as metal particles, such as gold, or polymeric beads, such as colored beads, or particles of carbon black. Other labels include, for example, enzymes, chromophores or fluorophores such as they are known in the art, particularly in immunoassays, or later developed. A populations of beads are provided in powdered form on the reagent zone, which can include a bibulous material, such as filter paper, glass fibers, nylon, or nitrocellulose. These reagents are reversibly bound to the reagent zone because they can be mobilized when placed in contact with a fluid, such as a fluid sample passing along a test strip.

In another embodiment of non-limiting optional embodiments, the reagent zone can include components of a signal producing system, for example, catalysts, such as enzymes, cofactors, electron donors or acceptors, and/or indicator compounds.

A reagent zone can also include compounds or molecules that may be necessary or desirable for optimal performance of the test, for example, buffers (preferably dry buffers or conditioners), stabilizers, surfactants, salts, reducing agents, or enzymes.

Test Results Determination Zone

A test results determination zone includes immobilized or not immobilized reagents that can detect the presence of the medical tested substance, drug, compound, or metabolite being tested for, such as but not limited to, drugs of abuse (e.g., illegal, controlled, etc., drug or compound), metabolites, and antibodies. Such reagents are preferably in a dry state and can be covalently immobilized, non-covalently immobilized, or not immobilized in a fluid state. A test result determination zone can include either or both of one or more drug, compound, or metabolite detection zones and one or more control zones.

Depending on the particular format and drug, compound, or metabolite being tested for, a variety of reagents can be provided at the test results determination zone. For example, the test results determination zone can include specific binding members such as antibodies, enzymes, enzymatic substrates, coenzymes, enhancers, second enzymes, activators, cofactors, inhibitors, scavengers, metal ions, and the like. One or more of the reagents provided at the test results determination zone can be bound to the test strip material. Test strips including such reagents are known in the art and can be adapted to the test device of the present invention.

In a preferred aspect of the present invention, the one or more medical, drug, compound, or metabolite detection zones of the test results determination zone include one or more immobilized (covalently or non-covalently immobilized) specific binding members that bind with one or more drugs, compound, or metabolite of interest, such as one or more drugs, hormones, antibodies, metabolites, or infectious agents, when the drugs, compound, or metabolite are also bound by specific binding members bound to a label as are provided in the reagent zone. Thus, in embodiments where the reagent zone contains one or more specific binding members for the analyte, the specific binding members of the reagent zone and medical, drug, compound, or metabolite detection zone should bind with different epitopes on the medical tested substance, drug, compound, or metabolite being tested for. For example, when a labeled specific binding member in the reagent zone binds with the medical tested substance, drug, compound, or metabolite, then the immobilized specific binding member in the medical tested substance, drug, compound, or metabolite detection zone should bind with another area of drug, compound, or metabolite. Thus, when the medical tested substance, drug, compound, or metabolite is present in the sample, the medical, drug, compound, or metabolite will bind the labeled anti-drug, compound, or metabolite, which carried along to the test result determination zone at the medical tested substance, drug, compound, or metabolite detection zone which binds with the immobilized anti-medical tested substance, drug, compound, or metabolite to provide a visual readout.

A medical test, drug, compound, or metabolite detection zone can include substrates which change in an optical property (such as color, chemiluminescence or fluorescence) when a drug, compound, or metabolite is present. Such substrates are known in the art, such as, but not limited to, 1,2-phenylenediamine, 5-aminosalicylic acid, 3,3',5,5'tetra methyl benzidine, or tolidine for peroxidase; 5-bromo-4-chloro-3-indolyl phosphate/nitroblue tetrazolium for alkaline phosphatase and 5-bromo-4-chloro-3-indolyl-beta-D-galactopyranoside, o-nitrophenyl-beta-D-galactopyranoside, napthol-AS-BI-beta-D-galactopyranoside, and 4-methyl-umbelliferyl-beta-D-galactopyranoside for beta galactosidase.

In embodiments where a medical tested substance, drug, compound, or metabolite is detected by a signal producing system, one or more components of the signal producing system, such as enzymes, substrates, and/or indicators, can be provided in the medical tested substance, drug, compound, or metabolite detection zone. Alternatively, the components of the signal producing system can be provided elsewhere in the test strip and can migrate to the medical tested substance, drug, compound, or metabolite detection zone.

Optionally, the test results determination zone can include an optional control zone. A control zone can be upstream from, downstream from, or integral with the medical tested substance, drug, compound, or metabolite detection zone of the test result determination zone. In the latter case, when drug, compound, or metabolite and control give a positive reaction, the control zone and/or drug, compound, or metabolite detection zone can form an indicia, such as a marking, indicator, or "+" sign for a positive reaction and a marking, indicator, "−" sign for a negative reaction based on the particular format of the assay, and the assay test strip or case or casing can also optionally include an indication or indication area that indicates that the one or more of the assays is not valid, either as the test or the control, optionally as a negative or positive control for one or more the assays as run on one or more of the test strips.

A control zone provides a result that indicates that the test on the test strip has performed correctly. In one preferred aspect of the present invention, the reagent zone includes a specific binding member that binds with a known drug, compound, or metabolite different from the medical tested substance, drug, compound, or metabolite being tested for. For example, a rabbit-IgG may be provided in the reagent zone. A control zone can include immobilized (covalently or non-covalently) anti-rabbit-IgG antibody. In operation, when the labeled rabbit-IgG in the reagent zone is carried to the test result determination zone and the control zone therein, the labeled rabbit-IgG will bind with the immobilized an anti-rabbit-IgG and form a detectable signal.

A control zone can include substrates which change in an optical property (such as color, chemiluminescence or fluorescence) when an optional substance is present.

In one preferred aspect of the present invention, the test strip can include a results determination zone that includes an optional and a drug, compound, or metabolite detection zone, and a sample adulteration control zone. In another aspect of the present invention, a test strip can include a results determination zone that optionally includes an optional, and optionally an adulteration control zone. A second test strip can include an adulteration control zone and optionally an optional. Preferably, this second test strip includes both an adulteration control zone and an optional, but that need not be the case. In the instance where one or more first test strips can be used to detect a drug, compound, or metabolite other than an adulteration drug, compound, or metabolite and one or more second test strips can be used to detect an adulteration analyte, the test strips can be provided as multiple test strips or test strips that detect multiple drugs, compounds or metabolites.

Processing Zones

When used herein "processing zones can include any or all of the above zones.

Orientation of Zones

A various zones of a test strip, including a sample application zone, one or more reagent zones, and one or more test result determination zones, including one or more drug, compound, or metabolite detection zones and optionally including one or more control and one or more adulteration zones, can be on a single strip of material, such as filter paper or nitrocellulose, or can be provided on separate pieces of material. A different zones can be made of the same or different material or a combination of materials, but preferably are selected from bibulous materials, such as filter paper, fiberglass mesh and nitrocellulose. A sample application zone preferably includes glass fibers, polyester or filter paper, the one or more reagent zones preferably include glass fibers, polyester or filter paper and the test results determination zone, including one or more drug, compound, or metabolite detection zones and optionally including one or more control, preferably include nitrocellulose.

Optionally, a fluid absorbing zone is included. A fluid absorbing zone preferably includes absorbent paper and is used to absorb fluid in a sample to drive fluid from the sample application zone through the reagent zone and the detection zone, which can optionally also include dry buffers or conditioning compositions.

Preferably, the zones are arranged as follows: sample application zone, one or more reagent zones, one or more test results determination zones, one or more control, one or more adulteration zones, and fluid absorbing zone. If the test results determination zone includes an optional, preferably it follows the medical tested substance, drug, compound, or metabolite detection zone of the test result determination zone. All of these zones, or combinations thereof, can be provided in a single strip of a single material. Alternatively, the zones are made of different materials and are linked together in fluid communication. For example, the different zones can be in direct or indirect fluid communication. In this instance, the different zones can be jointed end-to-end to be in fluid communication, overlapped to be in fluid communication, or be communicated by another member, such an adjoining material, which is preferably bibulous such as filter paper, fiberglass or nitrocellulose. In using a joining material, a joining material may communicate fluid from end-to-end joined zones or materials including such zones, end-to-end joined zones or materials including such zones that are not in fluid communication, or join zones or materials that include such zones that are overlapped (such as but not limited to from top to bottom) but not in fluid communication.

When and if a test strip includes an adulteration control zone, the adulteration control zone can be placed before or after the results determination zone. When an optional is present in the results determination zone on such a test strip, then the adulteration control zone is preferably before the control zone, but that need not be the case. In non-limiting optional embodiments where a test strip is an optional test strip for the determination of an adulteration drug, compound, or metabolite and/or an optional, then the adulteration control zone can be placed before or after the control zone, but is preferably before the control zone.

Methods of Detecting of a Drug, Compound, or Metabolite in a Sample

A device of non-limiting optional embodiments can be used to collect a sample, transfer the sample to a test strip sample receiving zone and optionally mix the sample with one or more reagents, such as dry buffer or conditioner. A sample or sample and one or more reagents can then be conducted to a test element within a test strip to detect one or more drugs, compounds, or metabolites in the sample, preferably a sample application zone of a test strip. A sample can be liquid or colloidal. Examples of liquid or fluid samples that can be applied to the test strip can include blood, serum, saliva, or urine.

To collect a sample a fluid or colloidal sample can be applied via various techniques, for example pipetting, pouring or by use of a dropper. Alternatively a sample collection device can be used to collect a sample and transfer the sample onto the test strip. A sample collection device can be of different structures but is preferably a swab. A swab can be used to collect the sample onto the swab head by different embodiments such as for example dipping, swiping or swabbing. A swab with sample can be applied to the test strip that can optionally contain one or more reagents, or with dry buffer added to the sample.

In a particular embodiment, the disclosure is directed to an automated, portable, and wireless lateral flow testing device drug testing platform for optical analysis of pre calibrated lateral flow testing devices for illegal or controlled substance drug, compound, and/or metabolite threshold testing assays utilizing a smart phone provided with or in a protective case with digital image recognition software algorithms for qualitative and/or quantitative data test analysis and result reporting in a customizable software suite, with integrated alternative test strip/casing positioning for calibrated/result markings for digital image analysis to provide drug testing results in real time using dry buffer or conditioning of saliva or body fluid samples for the drug test strips for one or more specified drugs, compounds, or metabolites thereof.

Non limiting optional embodiments optionally provides a portable drug testing platform for digital image capture and analysis of pre-calibrated/quantitation of lateral flow drug test strips using dry buffer or pre-conditioning of saliva or body fluid test samples. A platform can optionally include digital camera hardware with digital components that record the pre-calibrated/quantitative test strips optionally including active chemistry and specific for one or more drugs, compounds, or metabolites; dry buffer or conditioning media for preparing the test sample; software for interfacing with the user, and an image processing and computing device to interface with the digital camera.

In the particular embodiment, the system accepts a broad range of lateral flow testing devices. A test sample (e.g., saliva or body fluid) is taken from the person being tested and added to one or more of the test cartridge or the test strip that is provided with dry buffer or conditioners to set up the sample for addition to the test strip for testing. A lateral test strip or test cartridge is provided with the conditioned test sample at a designated area and the sample then continues by timing or indicator to the designated or proper position for interaction with the drug analysis components of the test strip to react the sample to provide the indication of a positive, negative, and/or threshold amount of the medical tested substance, drug, compound, or metabolite being tested by a particular test strip. A test strip or casing of the test strip is provided with calibration, sufficient test sample, and result indicator markings to show the result of the test for each test strip and corresponding drug, compound or metabolite being tested.

A system then continues the drug testing by taking a digital image of the sample conditioned and run on each test strip with the digital camera positioned, optionally, via the tester, case and/or housing. Illumination can optionally be provided by the digital camera or a separate illumination source. Digital image data of the test strip result, additional identifying information including one or more of identification of the person being tested, information about the tester, the location, the drug testing being done, and the like, and this image and other data is collected and stored in the digital camera, data memory storage, and/or a cloud based or separate data memory storage device. A digital image data is then processed using a host device (e.g. dedicated smart phone, PDA, laptop, cellular phone, or the like) using processing capabilities in conjunction with the software component of the system. Software pre-loaded onto the smart phone or processor provides the processing instructions and compares image analysis data to pre-defined calibration data, yielding a qualitative or quantitative result, e.g., but not limited to positive, negative, over or below one or more threshold concentrations or amounts, and the like. A system can interface with the host device through several different physical standards. These standards include industry standards such as Personal Computer Memory Card International Association (PCMCIA), Universal Serial Bus (USB), Serial, Secure Digital, BlueTooth™, one or a combination of optical, magnetic, or solid state data drives, Wi-Fi or other company specific standards such as the Handspring Springboard Platform™.

In another embodiment, software is automated for later flow test strip digital imaging for cross-field testing compatibility. This system can provide compatibility with a wide array of commercial or custom lateral flow strips. A system digitizes and objectively quantifies results from tests (such as test strips that can optionally be conventionally read by a human manually); stores original and modified digital image and data into memory for review; and enhances test processing by executing image processing algorithms.

A lateral flow test strip device, method or system can optionally provide wherein said drug or compound is optionally selected from one or more of alcohol, cocaine, methamphetamine, heroin, THC, PCP, psilocybin, opiate drugs, or other know drugs or illegal or controlled substances or derivatives thereof, e.g., as known in the art or as listed or described herein. According to non-limiting optional embodiments, the drug test strip device, system or method can be used to test for drugs, compounds, derivatives thereof, or plants or fungi from which they are derived from, which can include, but are not limited to, amphetamines (Amphetamine, dextroamphetamine and methamphetamine), alcohol, anabolic steroids, anorectic drugs (e.g., benzphetamine (Didrex®), diethylproprion (Tenuate®, Tepanil®), mazindol (Sanorex®, Mazanor®), phendimetrazine (Bontril®, Prelu-27®), and phentermine (Lonamin®, Fastin®, Adipex®), barbiturates (e.g., methohexital (Brevital®), thiamyl (Surital®) and thiopental (Pentothal®); amobarbital (Amyta®), pentobarbital (Nembutal®), secobarbital (Seconal®), Tuinal (amobarbital/secobarbital combination); butalbital (Fiorina®), butabarbital (Butisol®), talbutal (Lotusate®), and aprobarbital (Alurate®)); benzodiazepines (estazolam (ProSom®), flurazepam (Dalmane®), temazepam (Restoril®), triazolam (Halcion®); Midazolam (Versed®), alprazolam (Xanax®), chlordiazepoxide (Librium®), clorazepate (Tranxene®), diazepam (Valium®, halazepam (Paxipam®), lorzepam (Ativan®), oxazepam (Serax®), prazepam (Centrax®), and quazepam (Doral®); clonazepam (Klonopin®), clorazepate; Flunitrazepam (Rohypnol®), Zolpidem (Ambien®) and zaleplon (Sonata®)); butorphanol, buprenorphin, bufotenine, Cannibis (THC, marijuana, hashish, hash oil, hemp), chloral hydrate, coca leaf, cocaine, codeine, cocaine, depressants, dextropropoxyphen, DET, DOB, DOM, DXM, Ecstasy (MDMA), ephedra, fentanyl, flunitrazepam, foxy, GBL, GHB, glutethimide, hallucinogens (LSD), Opiates (e.g., heroin); hydrocodone, hydromorphone, ketamine, K2 spice, khat, LAAM, magic mushrooms (e.g., AET, psilocybin, psilocin, peyote), MDA, meperidine, meprobamate, mescaline, methadone, methamphetamine, methcathinone, methaqualone, meth labs, methylphenidate, morphine, narcotics, NEXUS, opium, opium poppy, oxycodone, oxycontin, paraldehyde, PCP, pentazocine, peyote, prescription drugs, ritalin, rohypnol, salvia divinorum, san pedro cacti, STP, thebaine, tryptamines, 1,4 butane diol, 2C-B, 5MeO-AMT, or derivatives or synthetic derivatives thereof.

A clinical monitoring, diagnosis or testing disease or condition can include any known type of test that can use a lateral flow testing device of the invention, e.g., by not limited to: at least one of an immune, infecteous, malignant, cardiovascular or other disease, in a cell, tissue, organ, animal, or patient including, but not limited to:

at least one immune related disease of condition, e.g., but not limited to at least one of, arthritis, gastric ulcer, inflammatory bowel disease, ulcerative colitis, allergic/atopic diseases, asthma, allergic rhinitis, eczema, dermatitis, conjunctivitis, transplants, organ transplant rejection, graft-versus-host disease, sepsis, trauma/hemorrhage, burns, ionizing radiation exposure, pancreatitis, adult respiratory distress syndrome, hepatitis, chronic inflammatory pathologies, Crohn's pathology, sickle cell anemia, diabetes, nephrosis, atopic diseases, hypersensitity reactions, allergic rhinitis, hay fever, rhinitis, conjunctivitis, endometriosis, urticaria, systemic anaphylaxis, dermatitis, pernicious anemia, hemolytic disease, type B insulin-resistant diabetes, asthma, type III hypersensitivity reactions, diabetes mellitus, hepatitis, cirrhosis, vasculitis, allograft rejection, drug sensitivity, osteoporosis, encephalomyelitis, cachexia, cystic fibrosis, chronic obstructive pulmonary disease (COPD), dermatologic conditions, psoriasis, alopecia, nephritis, acute renal failure, hemodialysis, uremia, toxicity, cytokine therapy, chemotherapy, radiation therapy See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference;

at least one cardiovascular disease or condition, including, but not limited to, at least one of myocardial infarction, congestive heart failure, stroke, ischemic stroke, hemorrhage, arteriosclerosis, atherosclerosis, restenosis, diabetic arteriosclerotic disease, hypertension, hypertension, shock, heart failure, coronary artery disease, cardiomyopathy, endocarditis, aneurysms, peripheral vascular disorders, venous diseases, venous thrombosis, varicose veins, reperfusion injury, and the like;

at least one infectious disease, including, but not limited to, at least one of: acute or chronic bacterial infection, acute and chronic parasitic or infectious processes, viral and fungal infections, HIV infection/HIV neuropathy, meningitis, hepatitis (e.g., A, B or C, or the like), peritonitis, pneumonia, hemolytic uremic syndrome/thrombolytic thrombocytopenic purpura, malaria, dengue hemorrhagic fever, leishmaniasis, leprosy, toxic shock syndrome, streptococcal myositis, gas gangrene, mycobacterium tuberculosis, mycobacterium avium intracellulare, pneumocystis carinii pneumonia, pelvic inflammatory disease, orchitis/epidydimitis, legionella, lyme disease, influenza a, epstein-barr virus, viral-associated hemaphagocytic syndrome, viral encephalitis/aseptic meningitis, and the like;

at least one malignant disease in a cell, tissue, organ, animal or patient, including, but not limited to, at least one of leukemia, myelodysplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, bladder cancer, breast cancer, colorectal cancer, endometrial cancer, head cancer, neck cancer, hereditary nonpolyposis cancer, Hodgkin's lymphoma, liver cancer, lung cancer, non-small cell lung cancer, ovarian cancer, pancreatic cancer, prostate cancer, renal cell carcinoma, testicular cancer, adenocarcinomas, sarcomas, malignant melanoma, hemangioma, metastatic disease, cancer related bone resorption, cancer related bone pain, and the like;

at least one neurologic disease, including, but not limited to, at least one of: neurodegenerative diseases, multiple sclerosis, migraine headache, AIDS dementia complex, demyelinating diseases; extrapyramidal and cerebellar disorders; hyperkinetic movement disorders, drug-induced movement disorders; hypokinetic movement disorders, such as Parkinson's disease; spinocerebellar degenerations, multiple systems degenerations; systemic disorders; demyelinating core disorders; and disorders of the motor unit; chronic alcoholism, and the like.

See, e.g., the Merck Manual, 17$^{th}$ Edition, Merck & Company, Rahway, N.J. (1999).

DESCRIPTION OF THE DRAWINGS

FIG. 1 is a top plan perspective view of one exemplary embodiment of a lateral flow assay testing device 30 according to the invention. The device has a sample receiving end (covered by case 34) and an opposite or sample display end. The device provides regions for sample flow and assay reactions along the length of the device. These regions include a sample conditioning or reagent pad 38 and a test strip region 40 the distal end of which is the results display region 42. Also shown is top vent 64c covered by removable film 74.

FIG. 2 is a bottom plan, perspective view of the assay device according to the embodiment shown in FIG. 1 and illustrating the first layer or platform upon which the layers of the device are built.

FIG. 3 is a perspective top plan view of the second half of the protective case 32 according to one exemplary embodiment of the invention.

FIG. 4 is an exploded top plan view of one exemplary embodiment according to the invention. As shown the assay device is built by providing multiple functional layers that provide the different parts needed to perform the assay. The first layer 44, provides a platform upon which the following layer are built. In this embodiment, the platform 44 includes a tongue like section 44a which has multiple sample windows 44b open therein and is sized to be easily placed in the mouth of a person to be tested by the test assay. The next or second layer, 46 provides a pattern for the assembly of portions of the test strip. Layer 46 also has a tongue-like section 46a that includes a window 46b therein communicating with sample windows 44b. Test strips 48 are then placed on the bed of layer 46 and a third layer 52 or frame is layered on top. Frame 52 also has a tongue section, 52a with a window 52b in communication with windows 44b and 46b for allowing sample transfer. Layer 52 also provides a window 52c delimiting the boundaries of the test strip region and a window 52d delimiting the boundary of a timer region.

Next, a wick 54 is provided is layered in the handle region 52a of layer 52. The wick 52 is a bibulous or porous absorbent material such as paper, nitrocellulose or the like which allows fluid entering through the sample receiving regions to enter the test assay device 30. A fourth frame or pattern layer 56 is then laid onto of and sandwiching wick 54. Frame member 56 includes a window 56b in the tongue region 56a of layer 56 there is also a window 56c in communication with wick 54 and providing fluid passage of a sample taken up by wick 54. Layer 56 also provide one or more reaction windows 56d providing precise placement and fluid communication of the test sample and reagents with the test strip 48. Also shown are one or more vents 56e which are in communication with the sample flow path. These vents may be V-shaped and positioned in layers immediately above or below the layers defining the fluid flow path and containing the bibulous material. The size of venting can effectively control the speed of movement of the sample fluid head through the fluid flow path.

A fifth frame member 60 is laded over layer 56. Layer 60 provides has a tongue 60a and provides a window 60b for fluid communication with sample wick 54, Layer 60 also provides a window 60c in fluid contact with wick 54 through hole 56c and a window 60d delimiting the boundaries of the test strips 48. Conditioning pad 62 sits on top of window 60c and is in fluid contact with reactions windows 56d. Layer 60, also provides a window 60d framing test strips 48.

A top layer 70 is applied on top of layer 60 and the conditioning pad. Frame member 70 has also has a tongue-like proximal end having one or more sample receiving windows 70b and (in this exemplary embodiment) a vent 70c in fluid communication with test strip 48. In the exemplary embodiment shown in FIG. 4 instruction for use, including a peel away or removable thin film which seals vent 70c.

Figure 5A:
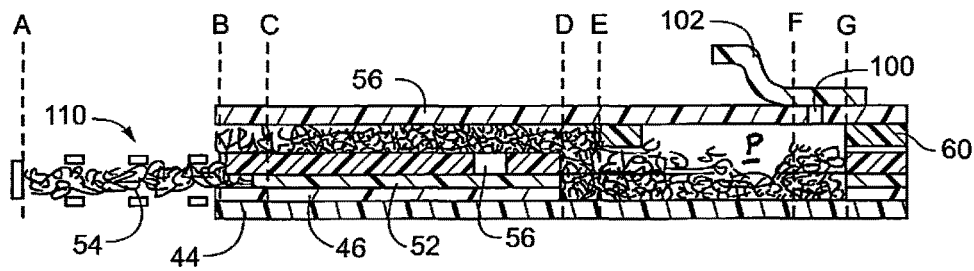
FIGS. 5A-F are cross sectional views of the embodiment of the lateral flow testing device illustrated in FIG. 4 a different stages of manufacture.

FIGS. 5A-5F are schematic cross sections through the lateral flow assay device 30 during its manufacture. FIG. 5A is a cross section along the length of the device through layers 44, 46, 52, 56, 60 and 70 as shown in FIG. 4. FIG. 5A shows the contiguous bibulous materials beginning with wick 54 and creating a continuous flow path 110 through the device. The flow path begins with section A-B which represents the sample receiving region and sample wick 54. Section B-C represents the flow transfer from the receiving region through an aperture in a framing member, such as, for example, hole 56c shown in FIG. 4. Also shown is conditioning region C-D which also include conditioning pad 62 (not shown). The flow is then transferred to the test strips 48 (not shown) through flow transfer region at D-E to enter reaction region E-G. Also shown in section E-G is an air chamber or pocket "P" extending through the reaction region. Section F-G comprises the results display region which also includes a vent 100 sealed by a thin film impeding member such as a pull tab 102. Fluid flow through the bibulous material is impeded by built up air pressure in the air pocket and the flow, and therefore the reaction will not proceed until the air pressure is released by removing pull tab 102 and opening vent 100.

Figure 5B:
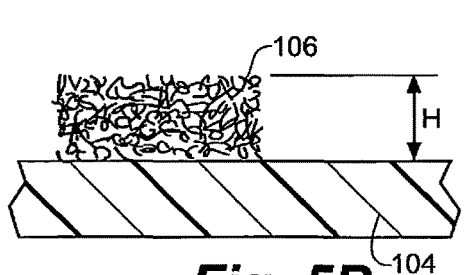
Figure 5C:
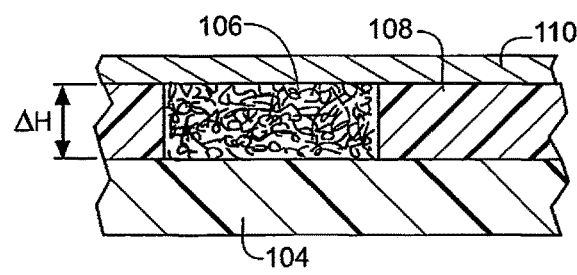

FIG. 5B is a schematic cross-section showing the layering of bibulous material 106 on a substrate 104. FIG. 5c shows the same substrate 104 with the same bibulous material 106 thereon but also encompassed by frame/layer 108 and overlaid by frame/layer 110. As shown in FIG. 5B, prior to the addition of layers 108 and 110, the bibulous material has a height or thickness "H". After the addition of further layers 108, 110, the bibulous material is slightly compress to a height ΔH which compression is less than 10%.

Figure 5D:
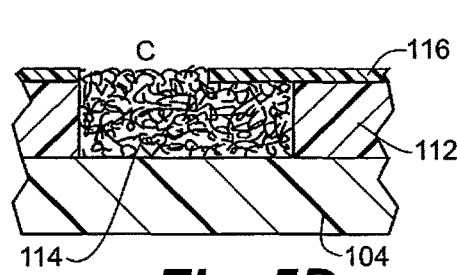
Figure 5E:
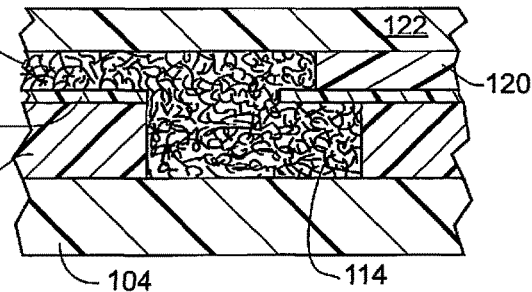

FIGS. 5D and 5E show the addition of further layers on the device and the continuation of the bibulous flow path. FIG. 5D shows a substrate 104 or first layer upon which a framing layer 112 is laid together with a bibulous material. A further layer 116 is then placed over bibulous material 114 and layer 112 except that layer 116 has a widow therein such that a portion of the bibulous material is not covered "C". FIG. 5E shows the same construct but with the addition of a second bibulous layer 118 surrounded by frame/layer 120 and covered by top layer 112. This diagram shows that due to the slight compression of the bibulous material and due to the widows in the framing members the adjoined bibulous material make a contiguous flow path through the layered device.

Figure 5F:
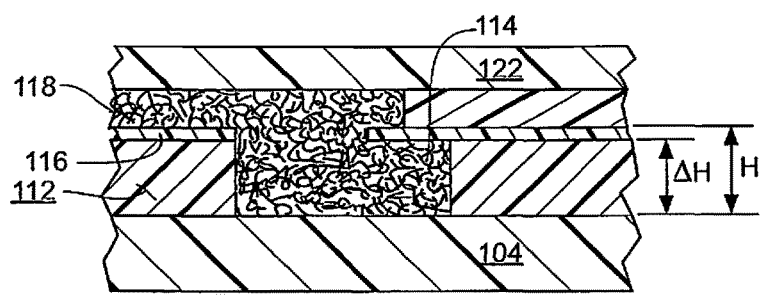

FIG. 5F illustrates the construct of FIG. 5E and showing that the compression ΔH provides for the continuous flow path through the contiguous bibulous materials.

Figure 6:
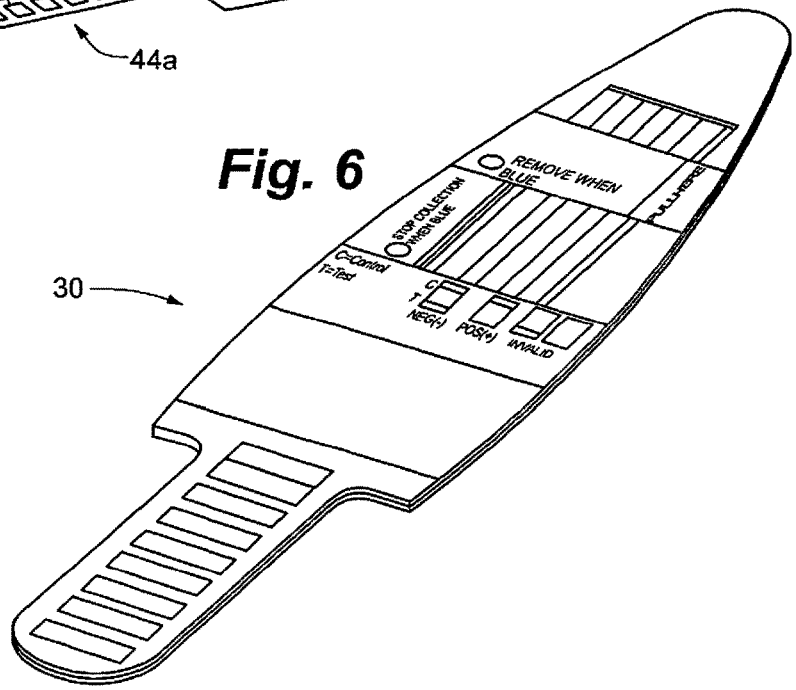
FIG. 6 is a top plan perspective view of the lateral flow testing device shown in FIGS. 4 and 5.

FIG. 6 is a perspective top plan view of the assembled device 30 according to one exemplary embodiment of the invention. Those of skill in the art will appreciate that, when the layer of the device are assembled, they are sealed with adhesive or the like so that the flow path and the movement of air into and out of the device is controlled.

FIG. 7 is a top plan perspective view of platform layer 44. Also shown are tongue like portion 44a and sample receiving windows 44b.

FIG. 8 is a top plan perspective view of second layer 46 also illustrating the tongue-like section.

FIG. 9 shows the placement of reaction components along the assay device from a proximal or receiving end at the tongue section 52a to a distal or diagnostic result display region 48 a. These components include a wick 54 at the sample receiving end, a timing strip 50 running alongside the test strips 48. The test strips include multiple regions including but not limited to a conjugation region 48a, a reaction region 48b and a results display region 48c.

FIG. 10 shows the fabrication of the device with the third window 52 added. As seen in this view the sample flow path is continued to include a transverse flow path 58 reflecting the width of the conditioning pad 62 which brings it in fluid communication with the wick 54.

FIG. 11 shows the inclusion of the fourth layer 56, which provides the frame work for directing sample flow from the conditioning pad 62 to the specific flow path of the test strip via opening 56d. Also shown is one or more vents 56e which allows air to enter the otherwise sealed device.

FIG. 12 shows the addition of the conditioning pad 62 spanning the area from the wick 54 end to the beginning of test strip 48.

FIG. 13 shows the addition of layer 60 to delimit the area of the conditioning pad 62 and test strips 48 and to bring conditioning pad into fluid contact with flow opening 56d.

FIG. 14 sows the final layer of the device 70 added with vent 64 provided, in this exemplary embodiment above and in fluid communication with the result display region 48c of test strip 48.

FIG. 15 shows the device with instructions 82 adhered to the sixth layer including instructions 82a that enough sample has been loaded and instruction 82b to remove the covering of the vent.

Figure 16:
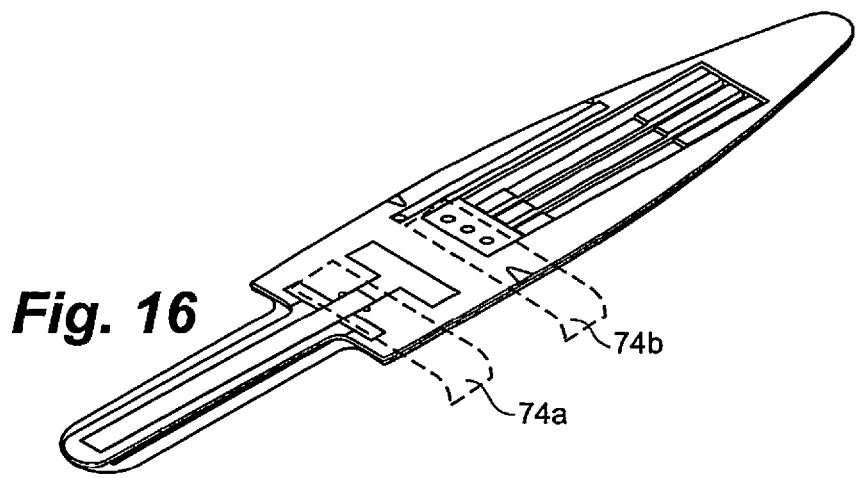
FIG. 16 illustrates some exemplary embodiments of the placement of impeding member films along the sample flow path of the lateral flow assay according to the invention.

FIG. 16 illustrates another exemplary embodiment of methods to interrupt fluid flow through the diagnostic device until such time as an impeding film is removed. Film 74a interrupts the flow pathway from wick 54 through flow hole 56c to conditioning pad 62. Film 74b interrupts the flow path from tad 62 through reaction holes 56d which lead to test strip lanes 48.

Figure 17:
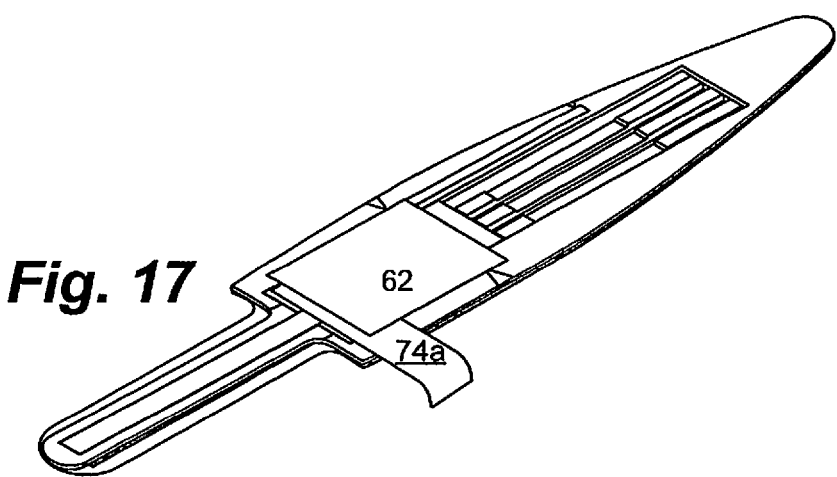
FIG. 17 illustrates the placement of the conditioning pad along the axis of flow travel and the interference of an impeding member.

FIG. 17 illustrates thin film impeding member 74a being juxtaposed between wick 54 and conditioning pad 62. As illustrated in this embodiment, a portion of the film remains outside the device allowing the user or other personnel to remove the film thereby restoring the fluid flow path and allowing the assay to progress to completion.

Figure 18:
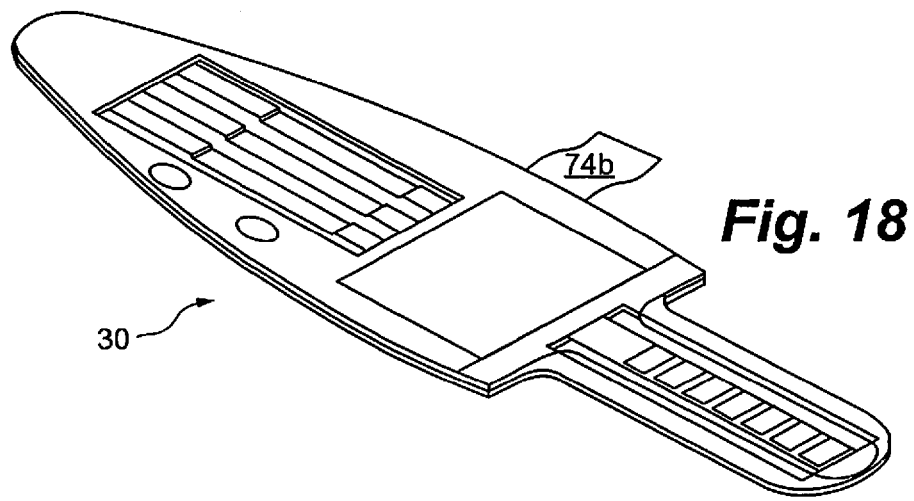
FIG. 18 illustrates an exemplary embodiment of a removable film along the sample flow path in an assembled assay device.

FIG. 18 illustrates thin film 74b juxtaposed between conditioning pad 62 and reaction holes 56d. As with thin film 74a, a portion of the film remains outside the device allowing the user or other personnel to pull the film from the device thereby allowing the assay to progress.

Referring to FIGS. 19-26, embodiments of the invention are illustrated in the context of a home pregnancy test device 200. A conventional test device is configured as in FIGS. 19 and 20, FIG. 20 illustrating the device with the top clam shell half removed showing the bottom clam shell half 201. Result window 202 and validation window 204 are open to the bibulous test processing material 206 including a test result display portion 207. The bibulous sample collection portion configured as a wick 208 is in contact engagement with the bibulous test processing material 206. FIGS. 21 and 22 illustrates a HCG test device 220 which is essentially similar to the device in FIGS. 19 and 20 with a thin film test process interrupter 224 with a pull tab 226 which optionally may have instructions 228 thereon. FIGS. 23 and 24 illustrates a HCG test device 230 which is essentially similar to the device in FIGS. 19 and 20 with a C-shaped clamp that compresses the bibulous test process material 234 and is removable or movable to uncompress the bibulous test process material and allow the test to proceed. FIGS. 25 and 26 illustrates another HCG test device 240 which is essentially similar to the device in FIGS. 19 and 20 with a rigid member configured as a rod 244 which extends through bosses 246 with holes such that the rod is held compressively against the bibulous test process material 248. The bibulous test process material is pinched between the lower clam shell half 255 and the rigid member 244. The rod can be removed in a transverse direction to the length of the device as indicated by the arrow 252 with a manual handle 256. FIG. 27 illustrates a test device 260 in a package 264 with instructions 266, and instructions 268 may be on the packaging 264. The instructions may relate to use of the delay or interrupter mechanism. In embodiments with a timer, the instructions may reference removal of the interrupter upon the timer providing a signal of a particular elapsed time period after the test was initiated, for example, after the sample is received in the sample receiving region or wick.

Those of skill in the art will appreciate that in one exemplary embodiment, the structure of the lateral flow assay testing device described herein provides for a continuous flow path of bibulous material provided in separate but contiguous regions of the device in which the bibulous layer are in fluid contact with each other thereby providing flow control of the timing and speed of the assay reaction. Further by assuring that the frames of the windows of the layers in the device are sealed, the flow can be controlled by the addition of vents along the flow path. Thus, in use, the test subject or user places the tongue-like section containing a wick in their mouth (or sample fluid). Saliva (or other sample fluid) is drawn into the wick and flows distally down the wick by diffusion. Upon entering the body of the device, the bibulous material of the wick ends and the sample is drawn through an aperture in a framing layer, such as but not limited to hole 56c (FIG. 4) to a separate contiguous components such as conditioning pad 62. As the sample flows or diffuses through the conditioning pad it mixes with reagents required for the reaction including buffers and the like. When the sample fluid diffuses through the filter it continues to diffuse across its concentration gradient by passing through another reaction aperture, such as those shows as 56d (FIG. 4). In the embodiment shown, apertures 56d align with test specific test strip lane shown at 48 including a timer or control lane which measures the sufficiency of the sample size of the reaction. Once the sample enters the test strip, the specific reaction and/or assays for which the test strip is designed are performed as the fluid sample continues to be drawn through the reaction region until it enters an area including an air pocket or cavity. Due to the pressure build up due to the resistance of air in the pocket, the fluid cannot migrate through the test strip. However, the user or administrator of the test, can then note the progress of the timing or control lane and when that lane indicates sufficient time has passed, a visual signal will appear in a control window such as 82a (FIG. 4). The collection control, sufficiency window indicates that sample no longer needs to be applied to the device. A second window, such as 82b provides a visual signal that sufficient time has passed allowing the reaction to be completed and that the user/administrator can remove the impeding film, letting the flow progress to the results section of the assay by opening the vent and releasing the air pressure in the cavity.

The following paragraphs enumerated consecutively from 1 through 73 provide for various aspects of the present invention. In one embodiment, in a first paragraph (1).

1. An elongate lateral flow assay testing device comprising:
   a body having a sample receiving end and an opposite end and comprising a plurality of laminated layers including a top layer and a bottom layer and plurality of window frame layers sandwiched therebetween, the plurality of window frame layers defining a plurality of interconnected containment regions whereby sample fluid can flow from the sample receiving end toward the opposite end, the regions comprising:
   a. a sample receiving region with a wick therein, the sample receiving region at the sample receiving end;
   b. a conditioning region downstream from and adjacent to the sample receiving region, the conditioning region having a conditioning pad therein;
   c. a reaction region with bibulous material downstream and adjacent to the conditioning region;
   d. a diagnostic result display region with bibulous material downstream and adjacent to the reaction region;
   the testing device further comprising a movable thin film impeding member in a laminated engagement with the body creating a sample fluid flow stop upstream of the diagnostic result display region, the thin film impeding member movable from an impeding position to a lesser impeding position whereby in the lesser impeding position the fluid flow moves beyond the fluid flow stop toward the diagnostic result display region.

2. The elongate lateral flow assay testing device of claim 1 wherein the fluid flow stop is provided by a vent positioned upstream from the diagnostic result display region and wherein the diagnostic display region is hermetically sealed downstream from the stop whereby the sample fluid flow is impeded from flowing into the diagnostic display region, the body having a vent extending into the reaction region and wherein the thin film impeding member is sealing and removably engaged with the body at and covering the vent, whereby the thin film impeding member may be peeled off opening the vent and allowing the sample fluid flow into the diagnostic result display region.

3. The elongate lateral flow assay testing device of claim 2 wherein the fluid flow stop is positioned upstream of the reaction region and the reaction region and the diagnostic result display region are contiguous.

4. The elongate lateral flow assay testing device of claim 1 wherein a fluid flow path is defined from the wick to the conditioning pad to the bibulous material in the reaction region to the bibulous material in the diagnostic display region, and wherein the thin film impeding member is in the fluid flow path intermediate the sample receiving region and the diagnostic result display region thereby defining the impeding position and the removal of the thin film impeding member out of the fluid flow path defines the lesser impeding position.

5. The elongate lateral flow assay testing device of claim 1 further comprising a capillary timer that provides a visual signal after a predetermined period of time from activation.

6. The elongate lateral flow assay testing device of claim 5 wherein the capillary timer comprising an elongate bibulous strip positioned in a timing region cavity defined in the body and in fluid communication with one of the wick and conditioning pad whereby the activation occurs when a sample is received in the sample receiving region.

7. The elongate lateral flow assay testing device of claim 5 or 6 wherein the device further has instructions associated therewith instructing users to take an action associated with the thin film impeding member when the visual signal of the capillary timer appears.

8. The elongate lateral flow assay testing device of claim 1 or 5 further comprising a sample sufficiency indicator visually viewable on the containment.

9. The elongate lateral flow assay testing device of claim 8 including instructions relating to stopping the sample collection.

10. A lateral flow assay testing device comprising:
    a. an elongated containment with a fluid sample receiving end, an opposite end;
    b. bibulous sample receiving material exposed at the sample receiving end;
    c. bibulous fluid sample processing material extending from the bibulous sample receiving material and extending lengthwise in the containment to a visual signal generating portion and defining a processing fluid flow path;
    d. separate elongate bibulous timer material connecting to the sample receiving material and having a fluid sample flow controlled portion and a visual signal generating portion opposite the flow controlled portion for generating a time signal after a time delay; and
  e. a switch initially set to one of impede or interrupt the processing fluid flow path, the switch manually switchable to a position providing increased fluid flow in the processing flow path.
11. The lateral flow assay testing device of claim 10 wherein a portion of the bibulous fluid sample processing material has a needed processing time and the separate elongate bibulous timer material is configured for providing the time signal a period of time at least equal to the needed processing time after the sample receiving material receives a fluid sample.
12. The lateral flow assay testing device of claim 10 or 11 wherein the switch comprises a removable vent closure sealing a vent that extends from an interior compartment containing a portion of the fluid flow path.
13. The lateral flow assay testing device of claim 12 wherein the vent closure comprises a film piece peelably removable from an exterior surface of the containment.
14. The lateral flow assay testing device of claim 10 or 11 wherein the switch comprises a member extending into and interrupting the processing flow path, the member retractable from the processing flow path by a portion exteriorly actuatable with respect to the containment.
15. The lateral flow assay testing device of claim 10 wherein the switch comprises a thin film member positioned in between and two portions of confronting bibulous material whereby when the thin film is in place the fluid sample is at least substantially blocked from flowing between the two portions and when the thin film member is removed the fluid sample has an increased flow capability between the two portions.
16. The lateral flow assay testing device of claim 10 wherein the switch comprises a thin film member movable between an impeding position and a less impeding position in the processing fluid flow path.
17. The lateral flow assay testing device of claim 10 wherein the switch comprises an exposed tab end for grasping and a fluid flow impeding end positioned in the fluid flow path.
18. The lateral flow assay testing device of claim 10, 11, 15, 16 wherein the containment is formed by a stack of laminated layers comprising an uppermost layer and a lowermost layer and a plurality of layers sandwiched therebetween, the plurality of layers sandwiched therebetween configured as stacked framing members defining at least one cavity for bibulous material.
19. The lateral flow assay testing device of claim 10 through 17 further comprising a lay with a v-shaped vent extending laterally into the processing fluid flow path providing a stop point for the fluid flow.
20. A lateral flow assay testing device comprising:
  a. an elongated containment with a fluid sample receiving end, an opposite end;
  b. bibulous sample receiving material exposed at the sample receiving end;
  c. bibulous fluid sample processing material extending from the bibulous sample receiving material and extending lengthwise in the containment to a visual signal generating portion defining a fluid sample processing flow path; and
  d. a timer actuatable with a visually readable portion on the containment, receiving material for actuation when a sample is received at the sample receiving material, the timer having a visual signal generating portion opposite the flow controlled portion for providing a visual signal after a time delay, the timer having a bibulous timing material and a fluid sample timer flow path separate from the fluid sample processing flow path.
21. The lateral flow assay testing device of claim 20 further comprising a switch initially set to one of impede or interrupt the processing fluid flow path, the switch manually switchable to a position providing increased fluid flow in the processing flow path.
22. The lateral flow assay testing device of claim 20 wherein a portion of the bibulous fluid sample processing material has a needed processing time and the timer is configured or configurable for providing visual signal a period of time at least equal to the needed processing time after the sample receiving material receives a fluid sample.
23. The lateral flow assay testing device of claim 20, 21, or 22 wherein the switch comprises a removable vent closure sealing a vent that extends from an interior compartment containing a portion of the fluid flow path.
24. The lateral flow assay testing device of claim 20, 21, or 22 wherein the switch comprises a removable blockage for the fluid sample processing flow path.
25. The lateral flow assay testing device of claim 20 further comprising an actuator that has a normal position of no fluid flow and when actuated allows fluid flow, the testing device further including directions referencing actuation of the actuator when the timer generates a signal.
26. A lateral flow assay testing device comprising:
  a. an elongated containment with a fluid sample receiving end, an opposite end;
  b. a bibulous sample receiving material exposed at the sample receiving end;
  c. a bibulous fluid sample processing material extending from the bibulous sample receiving material and extending lengthwise in the containment to a visual signal generating portion and defining a processing fluid flow path;
  d. a removable blocking member positioned to block or impede the processing fluid flow path, the blocking member having a portion exposed exteriorly of the containment for withdrawal of the blocking member.
27. The lateral flow assay testing device of claim 26 wherein the portion exposed exteriorly of the containment for actuation is configured as a pull tab.
28. The lateral flow assay testing device of claim 27 wherein the blocking member is a thin film portion sandwiched between two overlying bibulous material portions
29. The lateral flow assay testing device of claim 28 wherein the two overlying bibulous portions are under compression whereby when the blocking member is removed the bibulous portions extend towards one another.
30. The lateral flow assay testing device of claim 26 wherein the blocking member is a portion of a C-shaped clamp that pinches a portion of the bibulous material.
31. The lateral flow assay testing device of claim 26 wherein the blocking member is a rigid insert that extends past and pinches a portion of the bibulous material.
32. The lateral flow assay testing device of claim 26 wherein the bibulous sample processing material has been treated for detecting hCG.
33. The lateral flow assay testing device of any of claim 26 through 32 wherein the device comprises at least 6 layers laminated together.
34. The lateral flow assay testing device of any of claim 26 through 32 wherein no electrical circuitry is utilized in the device.

35. The lateral flow assay testing device of any of claim 26 through 32 further comprising a capillary timer connected to the bibulous sample receiving path and extending essentially parallel to the processing fluid flow path.

36. A lateral flow assay testing device comprising:
  a plurality of laminated layers including a top layer and a bottom layer and a plurality of fluid flow conduit regions defined therein for conducting the assay; the regions comprising:
  a. a fluid sample receiving region;
  b. a conditioning region downstream and in fluid connection with the fluid sample receiving region defining a fluid flow path for fluid sample to flow to the reagent region from the sample application region;
  c. a diagnostic result display region with a bibulous flow path from the reagent region to the diagnostic result display region;
  d. a movable flow path obstructing member thin film member positioned for the thin film to obstruct the flow between the sample receiving region and one of the reagent region and the diagnostic result display region, the movable flow path obstructing member movable from an obstructing position to a lesser obstructing position.

37. The lateral flow assay testing device of claim 36 wherein the blocking member is a C-shaped clamp 38. The lateral flow assay testing device of claim 36 wherein the blocking member is a rigid insert that extends past and pinches the bibulous flow path.

39. The lateral flow assay testing device of any of claim 36 through 38 further comprising a capillary timer connected to the bibulous sample receiving path and extending essentially parallel to the bibulous flow path.

40. The lateral flow assay testing device of claim 39 further comprising instructions associated with moving the movable device when the timer provides a specific indication.

41. A method of providing a user or test giver controllable delay for the processing of a fluid sample in a lateral flow assay test device, the method comprising removably pinching a bibulous portion of a fluid flow path of the test device.

42. The method of claim 41 further comprising utilizing providing a timer in the device for providing a signal as to when to unpinch the bibulous portion and a sufficiency indicator.

43. The method of claim 41 further comprising including bibulous material treated for detecting hCG 44. A method of delaying the processing of a fluid sample in an elongate lateral flow assay test device, the method comprising pinching a bibulous portion of a fluid flow path with a member extending transverse to the length of the device.

45. A method of providing a user controllable delay for the processing of a fluid sample in a lateral flow assay test device, the method comprising pinching a bibulous portion of a fluid flow path with a removable C-shaped clamp, the clamp removable for unpinching the bibulous portion thereby continuing or initiating the processing.

46. The method of claim 45 further comprising providing packaging and instruction in the packaging or on the device associated with using the timer.

47. The method of claim 44 or 45 further comprising a sufficiency indicator.

48. A method of assembling a lateral flow assay test device comprising:
  a. layering one or more framing layers over a base layer to define a window for receiving a bibulous pad, the window having a depth;
  b. inserting an uncompressed bibulous pad with a height that is greater than the depth of the window on the base and seating the pad on the base layer;
  c. layering a cover layer over the window with the pad therein thereby compressing at least a portion of the bibulous pad; and
  d. laminating together the base layer, one or more framing layers, and cover layers.

49 The method of claim 48 wherein the depth of the window is 90 percent or more than the height of the uncompressed bibulous pad.

50. The method of claim 48 or 49 wherein the cover layer has an opening above the bibulous pad whereby the cover layer is sized that a portion of the bibulous pad extends therein.

51. The method of claim 50 wherein the bibulous pad is a first bibulous pad and a second bibulous pad is placed on the cover layer at the opening and the second bibulous pad is in fluid communication with the first bibulous pad.

52. The method of claim 50 wherein the bibulous pad is a first bibulous pad and a second bibulous pad is placed on the cover layer at the opening and the second bibulous pad further comprising adding an additional framed layer for surrounding the second bibulous pad and an additional cover layer that provides a containment for the second bibulous layer, the second bibulous layer being compressed by the second framed layer whereby the first bibulous pad and second bibulous pad extend toward each other in the opening.

53. The method of claim 48 further comprising interleaving a thin film pull strip between a pair of adjacent bibulous pads without affixing the thin film pull strip therein, whereby a fluid sample flow path is interrupted and the interruption may be removed by the removal of the thin film pull strip from between the pair of adjacent bibulous pads.

54. The method of claim 48 further comprising providing a vent hole in the cover layer and sealingly closing the cover layer with an adhesively attached closure member.

55. The method of claim 54 wherein the closure member is a thin flexible film and the method further comprises layering the thin flexible film on the cover layer with an exposed nonattached tab portion for removal of the thin flexible film.

56. A method of manufacturing lateral flow assay test devices comprising laminating a plurality of layers together including an upper layer that partially defines a chamber for a bibulous material, the upper layer having a vent hole therein for releasing fluid sample and removably affixing a further layer on the upper layer for sealing the vent hole, the further layer removable for unsealing the vent hole.

65. The method of claim 64 further comprising utilizing at least 6 layers.

66. A method of manufacture of lateral flow assay test device comprising interleaving a thin film pull strip between a pair of adjacent bibulous pads without affixing the thin film pull strip therein, whereby a fluid sample flow path is interrupted and the interruption may be removed by the removal of the thin film pull strip from between the pair of adjacent bibulous pads.

67. A lateral flow assay test device comprising at least five laminated layers defining a sample fluid flow path with bibulous material therein and further comprising a interleaved thin film pull strip between a pair of adjacent bibulous pad portions with a pull tab for removing the thin film pull strip from between the pair of adjacent bibulous pad portions.

68. The lateral flow assay testing device of claim 67 further comprising a capillary timer connected to a sample receiving region and having a timer flow path and extending separate from the sample fluid flow path.

69. The lateral flow assay testing device of claim 67 further comprising a sufficiency indicator in the timer flow path.

70. The lateral flow assay testing device of any of claims 67 to 69 further comprising instructions associated with pulling the pull tab when the timer provides a specific indication.

71. A lateral flow assay test device comprising at least five laminated layers defining a sample fluid flow path with bibulous material therein and further comprising a interleaved thin film pull strip between a pair of adjacent bibulous pad portions with a pull tab for removing the thin film pull strip from between the pair of adjacent bibulous pad portions.

72. A method of manufacturing lateral flow assay test devices comprising laminating a plurality of layers together including an upper layer that partially defines a chamber for a bibulous material, the upper layer having a vent hole therein for releasing fluid sample and removably affixing a further layer on the upper layer for sealing the vent hole, the further layer removable for unsealing the vent hole.

73. The method of claim 72 further comprising venting a fluid flow path up stream from the chamber thereby providing a fluid stop.

The above references in all sections of this application are herein incorporated by references in their entirety for all purposes.

All of the features disclosed in this specification (including the references incorporated by reference, including any accompanying claims, abstract and drawings), and/or all of the steps of any method or process so disclosed, may be combined in any combination, except combinations where at least some of such features and/or steps are mutually exclusive.

Each feature disclosed in this specification (including references incorporated by reference, any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment (s). The invention extends to any novel one, or any novel combination, of the features disclosed in this specification (including any incorporated by reference references, any accompanying claims, abstract and drawings), or to any novel one, or any novel combination, of the steps of any method or process so disclosed The above references in all sections of this application are herein incorporated by references in their entirety for all purposes.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative aspects. The above described aspects embodiments of the invention are merely descriptive of its principles and are not to be considered limiting. Further modifications of the invention herein disclosed will occur to those skilled in the respective arts and all such modifications are deemed to be within the scope of the invention.

Having shown and described various embodiments, further adaptations of the methods and systems described herein may be accomplished by appropriate modifications by one of ordinary skill in the art without departing from the scope of this disclosure. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of whatever claims recite the invention, and is understood not to be limited to the details of structure and operation shown and described in the description.

What is claimed is:

1. An elongate lateral flow assay testing device comprising:
    a body having a sample receiving end and an opposite end and comprising a plurality of laminated layers including a top layer and a bottom layer and a plurality of window frame layers sandwiched therebetween, the plurality of window frame layers defining a plurality of interconnected containment regions whereby sample fluid can flow from the sample receiving end toward the opposite end, the regions comprising:
        a. a sample receiving region with a wick therein, the sample receiving region at the sample receiving end;
        b. a conditioning region downstream from and adjacent to the sample receiving region, the conditioning region having a conditioning pad therein;
        c. a reaction region with bibulous material downstream and adjacent to the conditioning region;
        d. a diagnostic result display region with bibulous material downstream and adjacent to the reaction region;
    the testing device further comprising a movable thin film impeding member in a laminated engagement with the body creating a sample fluid flow stop upstream of the diagnostic result display region, the thin film impeding member movable from an impeding position to a lesser impeding position whereby in the lesser impeding position the fluid flow moves beyond the fluid flow stop toward the diagnostic result display region,
    wherein the fluid flow stop is provided by a vent positioned upstream from the diagnostic result display region and wherein the diagnostic display region is hermetically sealed downstream from the stop whereby the sample fluid flow is impeded from flowing into the diagnostic display region, the body having a vent extending into the reaction region and wherein the thin film impeding member is sealing and removably engaged with the body at and covering the vent, whereby the thin film impeding member may be peeled off opening the vent and allowing the sample fluid flow into the diagnostic result display region.

2. The elongate lateral flow assay testing device of claim 1, wherein the fluid flow stop is positioned upstream of the reaction region and the reaction region and the diagnostic result display region are contiguous.

3. The elongate lateral flow assay testing device of claim 1 wherein a fluid flow path is defined from the wick to the conditioning pad to the bibulous material in the reaction region to the bibulous material in the diagnostic display region, and wherein the thin film impeding member is in the fluid flow path intermediate the sample receiving region and the diagnostic result display region thereby defining the impeding position and the removal of the thin film impeding member out of the fluid flow path defines the lesser impeding position.

4. The elongate lateral flow assay testing device of claim 1 further comprising a capillary timer that provides a visual signal after a predetermined period of time from activation.

5. The elongate lateral flow assay testing device of claim 4 wherein the capillary timer comprising an elongate bibulous strip positioned in a timing region cavity defined in the body and in fluid communication with one of the wick and conditioning pad whereby the activation occurs when a sample is received in the sample receiving region.

6. The elongate lateral flow assay testing device of claim 4 wherein the device further has instructions associated therewith instructing users to take an action associated with the thin film impeding member when the visual signal of the capillary timer appears.

* * * * *